United States Patent
Slowing et al.

(10) Patent No.: US 9,556,088 B2
(45) Date of Patent: Jan. 31, 2017

(54) ADSORBENT CATALYTIC NANOPARTICLES AND METHODS OF USING THE SAME

(71) Applicant: Iowa State University Research Foundation, Inc., Ames, IA (US)

(72) Inventors: Igor Ivan Slowing, Ames, IA (US); Kapil Kandel, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 976 days.

(21) Appl. No.: 13/691,181

(22) Filed: Nov. 30, 2012

(65) Prior Publication Data
US 2014/0155669 A1 Jun. 5, 2014

(51) Int. Cl.
*C07C 7/12* (2006.01)
*C07C 1/22* (2006.01)
(Continued)

(52) U.S. Cl.
CPC ............. *C07C 7/12* (2013.01); *B01J 27/1853* (2013.01); *B01J 29/0308* (2013.01); *B01J 29/0325* (2013.01); *B01J 29/0333* (2013.01); *B01J 29/0341* (2013.01); *B01J 31/08* (2013.01); *B01J 31/10* (2013.01); *B01J 31/1616* (2013.01); *B01J 35/0033* (2013.01); *B01J 35/1061* (2013.01); *C07C 1/2078* (2013.01); *C07C 1/22* (2013.01); *C10G 3/44* (2013.01); *C10G 3/45* (2013.01); *C10G 3/48* (2013.01); *C10G 3/50* (2013.01); *C10G 25/003* (2013.01); *C10G 25/06* (2013.01); *C10G 45/06* (2013.01); *B01J 35/0013* (2013.01); *B01J 35/1019* (2013.01);
(Continued)

(58) Field of Classification Search
None
See application file for complete search history.

(56) References Cited

U.S. PATENT DOCUMENTS

| | | | |
|---|---|---|---|
| 4,279,756 A | 7/1981 | Weiss et al. | |
| 4,554,390 A | 11/1985 | Curtain et al. | |

(Continued)

FOREIGN PATENT DOCUMENTS

| | | |
|---|---|---|
| JP | 2006069824 A | 3/2006 |
| WO | WO-0132308 A1 | 5/2001 |

(Continued)

OTHER PUBLICATIONS

"U.S. Appl. No. 12/698,656, Notice of Allowance mailed Sep. 18, 2012", 10 pgs.

(Continued)

*Primary Examiner* — Joseph D Anthony
(74) *Attorney, Agent, or Firm* — Schwegman Lundberg & Woessner, P.A.

(57) ABSTRACT

The present invention provides an adsorbent catalytic nanoparticle including a mesoporous silica nanoparticle having at least one adsorbent functional group bound thereto. The adsorbent catalytic nanoparticle also includes at least one catalytic material. In various embodiments, the present invention provides methods of using and making the adsorbent catalytic nanoparticles. In some examples, the adsorbent catalytic nanoparticles can be used to selectively remove fatty acids from feedstocks for biodiesel, and to hydrotreat the separated fatty acids.

19 Claims, 8 Drawing Sheets

(51) Int. Cl.

| | | |
|---|---|---|
| B01J 31/12 | (2006.01) | |
| C07C 1/207 | (2006.01) | |
| C10G 25/00 | (2006.01) | |
| C10G 25/06 | (2006.01) | |
| C10G 45/06 | (2006.01) | |
| C10G 3/00 | (2006.01) | |
| B01J 31/08 | (2006.01) | |
| B01J 31/10 | (2006.01) | |
| B01J 31/16 | (2006.01) | |
| B01J 27/185 | (2006.01) | |
| B01J 29/03 | (2006.01) | |
| B82Y 30/00 | (2011.01) | |
| B01J 35/00 | (2006.01) | |
| B01J 35/10 | (2006.01) | |
| B01J 37/02 | (2006.01) | |

(52) U.S. Cl.
CPC ........ *B01J 35/1023* (2013.01); *B01J 37/0203* (2013.01); *B01J 37/0207* (2013.01); *B01J 37/0209* (2013.01); *B01J 2231/641* (2013.01); *B82Y 30/00* (2013.01); *C07C 2521/08* (2013.01); *C07C 2523/755* (2013.01); *C10G 2300/1011* (2013.01); *Y02E 50/13* (2013.01); *Y02P 20/52* (2015.11)

(56) References Cited

U.S. PATENT DOCUMENTS

| | | | |
|---|---|---|---|
| 7,550,634 B2 | 6/2009 | Yao et al. | |
| 7,625,490 B2 | 12/2009 | Cort | |
| 8,039,682 B2 | 10/2011 | McCall et al. | |
| 8,226,740 B2 | 7/2012 | Chaumonnot et al. | |
| 8,361,623 B2* | 1/2013 | Lin | B01D 15/08 423/335 |
| 8,435,912 B2 | 5/2013 | Chaumonnot et al. | |
| 8,828,705 B1* | 9/2014 | Lin | 423/335 |
| 9,359,396 B2* | 6/2016 | Chaix | B05D 7/00 |
| 2006/0018966 A1 | 1/2006 | Lin et al. | |
| 2006/0154069 A1 | 7/2006 | Lin et al. | |
| 2008/0021232 A1 | 1/2008 | Lin et al. | |
| 2008/0072705 A1* | 3/2008 | Chaumonnot | B01J 23/002 75/338 |
| 2008/0175783 A1 | 7/2008 | Park et al. | |
| 2009/0283442 A1* | 11/2009 | McCall | C10G 3/46 208/15 |
| 2010/0133147 A1* | 6/2010 | Chaumonnot | B01J 23/20 208/144 |
| 2010/0196971 A1 | 8/2010 | Lin et al. | |
| 2013/0012758 A1* | 1/2013 | Chen | A61L 27/10 600/12 |
| 2014/0135478 A1* | 5/2014 | Chaix | B05D 7/00 530/333 |
| 2014/0155670 A1* | 6/2014 | Slowing | C07C 1/22 585/733 |

FOREIGN PATENT DOCUMENTS

| | | |
|---|---|---|
| WO | WO-2004054708 A2 | 7/2004 |
| WO | WO-2008060571 A2 | 5/2008 |
| WO | WO-2009017425 A1 | 2/2009 |
| WO | WO-2010088001 A2 | 8/2010 |
| WO | WO-2010088001 A3 | 12/2010 |

OTHER PUBLICATIONS

"U.S. Appl. No. 12/698,656, Preliminary Amendment mailed Apr. 13, 2010", 6 pgs.
"U.S. Appl. No. 12/698,656, Response filed Aug. 22, 2012 to Restriction Requirement mailed May 31, 2012", 7 pgs.
"U.S. Appl. No. 12/698,656, Restriction Requirement mailed May 31, 2012", 11 pgs.
"International Application Serial No. PCT/US2010/000289, International Preliminary Report on Patentability mailed Aug. 11, 2011", 20 pgs.
"International Application Serial No. PCT/US2010/000289, Invitation to Pay Additional Fee mailed Jun. 21, 2010", 13 pgs.
"International Application Serial No. PCT/US2010/000289, Search Report mailed Sep. 14, 2010", 12 pgs.
"International Application Serial No. PCT/US2010/000289, Search Report mailed Oct. 22, 2010", 12 pgs.
"International Application Serial No. PCT/US2010/000289, Written Opinion mailed Sep. 14, 2010", 18 pgs.
"International Application Serial No. PCT/US2010/000289, Written Opinion mailed Oct. 22, 2010", 18 pgs.
Capasso, J. M., et al., "A colorimetric assay for determination of cell viability in algal cultures", Biomolecular Engineering, 20(Issues 4-6), (2003), 4-6.
Cazin, C. S. J., et al., "Versatile Methods for the Synthesis of Si(OR)sub 3-Functionalised Imidazolium Salts, Potential Precursors for Heterogeneous NHC Catalysts and Composite Materials", Synthesis 2005, No. 4, (2005), 622-626.
Cha, S., et al., "Colloidal Graphite-Assisted Laser Desorption/Ionization Mass Spectrometry and MSn of Small Molecules. 1. Imaging of Cerebrosides Directly from Rat Brain Tissue", Analytical Chemistry, 79(6), (2007), 2373-2385.
Chisti, Y., "Biodiesel from microalgae", Biotechnology Advances, 25, (2007), 294-306.
Dayananda, C., et al., "Autotrophic cultivation of Botryococcus braunii for the production of hydrocarbons and exopolysaccharides in various media", Biomass & Bioenergy, 31, (2007), 87-93.
Gadenne, B., et al., "Supported ionic liquids ordered mesoporous silicas containing covalently linked ionic species", Chemical Communications, 15, (2004), 1768-1769.
Hall, S. R., et al., "Template-directed synthesis of bi-functionalized organo-MCM-41 and phenyl-MCM-48 silica mesophases", Chem. Commun., (1999), 201-202.
Herrero, M. A., et al., "Recent Advances in the Covalent Functionalization of Carbon Nanotubes", Mol. Cryst. Liq. Cryst., 483, (2008), 21-32.
Hirsch, A., et al., "Functionalization of Carbon Nanotubes", Topics in Current Chemistry—Functional Molecular Nanostructures, vol. 245, (2007), 3-57.
Kim, T.-W., et al., "Structurally Ordered Mesoporous Carbon Nanoparticles as Transmembrane Delivery Vehicle in Human Cancer Cells", Nano Letters, 8(11), (2008), 3724-3727.
Leon-Banares, R., et al., "Transgenic microalgae as green cell-factories", Trends in Biotechnology, 22(1), (2004), 45-52.
MacQuarrie, D. J, "Organically modified hexagonal mesoporous silicas—Clean of high loading and non-catalytic second groups on catalytic activity of amine-derivatised materials", Green Chemistry, vol. 1, No. 4, DDOI: 10.1039/a904692e, (Sep. 6, 1999), 195-198.
Nepal, D., et al., "Chapter 4—Functionalization of Carbon Nanotubes", Functional Nanomaterials, Geckeler, K. E., et al., Editors, American Scientific Publishers, (2006), 57-79.
Pan, C., et al., "Carbon Nanotubes as Adsorbent of Solid-Phase Extraction and Matrix for Laser Desorption/Ionization Mass Spectrometry", J. Am. Soc. Mass Spectrom., 16, (2005), 263-270.
Pan, C., et al., "Using Oxidized Carbon Nanotubes as Matrix for Analysis of Small Molecules by MALDI-TOF MS", J. Am. Soc. Mass Spectrom., 16, (2005), 883-892.
Soeng, H., "Controlling the Selectivity of Competitive Nitroaldol Condensation by Using Bifunctionalized Mesoporous silica Nanosphere-Based Catalytic System", Journal of the American Chemical Society, vol. 126, No. 4, (Sep. 1, 2004), 1010-1011.
Udayakumar, S., et al., "Imidazolium derivatives functionalized MCM-41 for catalytic conversion of carbon dioxide to cyclic carbonate", Catalysis Communications, 10(5), (2009), 659-664.
Van Meter, D. S., et al., "Characterization of surface-confined ionic liquid stationary phases: impact of cation and anion identity on retention", Analytical and Bioanalytical Chemistry 393(1), (2008), 283-294.

(56) References Cited

OTHER PUBLICATIONS

Zhang, H., et al., "Colloidal Graphite-Assisted Laser Desorption/Ionization MS and MSn of Small Molecules. 2. Direct Profiling and MS Imaging of Small Metabolites from Fruits", Analytical Chemistry, 79(17), (2007), 6575-6584.
Zhila, N. O., et al., "Effect of Nitrogen Limitation on the Growth and Lipid Composition of the Green Alga Botryococcus braunii Kutz IPPAS H-252", Russian Journal of Plant Physiology, vol. 52(3), (2005), 311-319.
"U.S. Appl. No. 14/015,206, Response filed Nov. 23, 2015 to Restriction Requirement mailed Oct. 9, 2015", 7 pgs.
"U.S. Appl. No. 14/015,206, Restriction Requirement mailed Oct. 9, 2015", 8 pgs.
"U.S. Appl. No. 14/015,206, Non Final Office Action mailed Mar. 11, 2016", 9 pgs.
"U.S. Appl. No. 13/300,343, Non Final Office Action mailed Jul. 13, 2013", 8 pgs.
"U.S. Appl. No. 13/300,343, Notice of Allowance mailed Apr. 2, 2014", 9 pgs.
"U.S. Appl. No. 13/300,343, PTO Response to Rule 312 Communication mailed Jul. 29, 2014", 2 pgs.
"U.S. Appl. No. 13/300,343, Response filed Mar. 14, 2013 to Restriction Requirement mailed Feb. 21, 2013", 7 pgs.
"U.S. Appl. No. 13/300,343, Response filed Sep. 12, 2013 to Non Final Office Action mailed Jul. 3, 2013", 9 pgs.
"U.S. Appl. No. 13/300,343, Restriction Requirement mailed Feb. 21, 2013", 9 pgs.
Bargiel, Jeffrey T., "Commercialization of Lateral Displacement Array for Dewatering of Microalgae", Submitted in partial fulfillment of the requirements for the degree of Master of Science Thesis Committee: Robert Brown, Ph.D. J. Kevin Berner, Ph.D. Edward Caner Cyrus Taylor, Ph.D. Christopher Lane, Ph.D. Department of Physics Case Western Reserve Univer, (May 2009), 53 pgs.
Chan, W. C, et al., "Quantum dot bioconjugates for ultrasensitive nonisotopic detection", Science, 281(5385), (Sep. 25, 1998), 2016-8.
Chen, Y. M., et al., "Flotation removal of algae from water", Colloids and Surfaces B: Biointerfaces, 12(1), (Oct. 15, 1998), 49-55.
Divakaran, Ravi, et al., "Flocculation of algae using chitosan", Journal of Applied Phycology, 14(5), (2002), 419-422.
Doadrio, J. C., et al., "Functionalziation of mesoporous materials with long alkyl claims as a strategy for controlling drug delivery pattern", Journal of Material Chemistry, 16, (2006), 462-466.
Doyle, P. S, et al., "Self-assembled magnetic matrices for DNA separation chips.", Science, 295(5563), (Mar. 22, 2002), 2237.
Girt, Supratim, et al., "Stimuli-Responsive Controlled-Release Delivery System Based on Mesoporous Silica Nadorods Capped with Magnetic Nanoparticles", Angew. Chem. Int. Ed. 2005, 44, (2005), 5038-5044.
Gu, H., et al., "Using Biofunctional Magnetic Nanoparticles to Capture Vancomycin-Resistant Enterococci and Other Gram-Positive Bacteria at Ultralow Concentration", J. Am. Chem. Soc., 125(51), (2003), 15702-15703.
Hirsch, A., et al., "Functionalization of Carbon Nanotubes", Topics in Current Chemistry—Functional Molecular Nanostructures, vol. 245, (2005), 193-237.
Hung, Yung-Tse, et al., "Algae Harvest Energy Conversion", Handbook of Environmental Engineering, vol. 11: Environmental Bioengineering, (2010), 723-741.
Linton, Peter, et al., "Growth and Morphology of Mesophorous SBA-15 Particles", Chem. Mater. 20, (Apr. 10, 2008), 2878-2880.
Middlebrooks, E. Joe, et al., "Techniques for Algae Removal from Wastewater Stabilization Ponds", Journal (Water Pollution Control Federation), 46(12), (Dec. 1974), 2676-2695.
Uduman, Nyomi, et al., "Dewatering of microalgal cultures: A major bottleneck to algae-based fuels", Journal of Renewable and Sustainable Energy, 2, (2010), 012701-15.
Wang, J., et al., "Superparamagnetic Fe2O3 Beads-CdSe/ZnS Quantum Dots Core-Shell Nanocomposite Particles for Cell Separation", Nano Lett., 4(3), (2004), 409-413.
Xu, C., et al., "Dopamine as a Robust Anchor to Immobilize Functional Molecules on the Iron Oxide Shell of Magnetic Nanoparticles", J. Am. Chem. Soc., 126(32), (2004), 9938-9939.
Yiu, H H P, et al., "Synthesis of novel magnetic iron metal-silica (Fe-SBA-15) and magnetite-silica (Fe3O4-SBA-15) nanocomposites with a high iron content using temperature-programed reduction", Nanotechnology 19(25), (2008), 7 pgs.
Zhang, Xuezhi, et al., "Harvesting algal biomass for biofuels using ultrafiltration membranes.", Bioresour Technol., 101(14), (Jul. 2010), 5297-304.
Zheng, L., et al., "Magnetic Hollow Spheres of Periodic Mesoporous Organosilica and Fe3O4 Nanocrystals: Fabricaion and Structure Control", Advanced Materials, vol. 20, No. 4 (2008), 805-809.
"U.S. Appl. No. 14/015,206, Response filed Jun. 6, 2016 to Non Final Office Action mailed Mar. 11, 2016", 42 pgs.

\* cited by examiner

ADSORBENT CATALYTIC NANOPARTICLES AND METHODS OF USING THE SAME

STATEMENT OF GOVERNMENT SUPPORT

This invention was made with Government support under contract no. DE-AC02-07CH11358 awarded by the U.S. Department of Energy. The U.S. Government has certain rights in this invention.

BACKGROUND OF THE INVENTION

Petroleum-derived solvents and fuels are of environmental concern and are under legislative to be replaced by biodegradable substitutes that afford reduced environmental impact. Unpredictable petroleum prices and the increasing desire for energy independence and security have led to burgeoning research activities directed toward developing a variety of alternative fuels. Among these new fuels, biodiesel is a biodegradable, nontoxic diesel that can be produced by transesterification of various oil feedstocks, including vegetable oils, animal fats, algal oils, and restaurant waste oils. Examples of biodiesel can include fatty acid $C_{1-5}$ alkyl esters, such as soy diesel (methyl soyate), rapeseed methyl ester, and various vegetable and animal fat methyl esters. Biodiesel has been accepted worldwide as a viable alternative to traditional petroleum-derived solvents and fuels. Free fatty acids in the feedstocks for bio-diesel production can negatively affect the process and resulting product. For example, free fatty acids can react with catalysts used for transesterification, forming soaps and consuming catalyst. The efficiency and efficacy of biodiesel production can be greatly increased by reducing the concentration of free fatty acid in the feedstock.

Catalysts are essential materials in a wide variety of useful and important chemical reactions. Generally, catalysts are unselectively exposed to materials in a chemical reaction. Therefore, a molecule at lower concentration with a particular reactivity with the catalyst has a lower chance of undergoing the chemical change caused by the catalyst than a different molecule at a higher concentration having the same reactivity with the catalyst.

SUMMARY OF THE INVENTION

In various embodiments, the present invention provides an adsorbent catalytic nanoparticle. The adsorbent catalytic nanoparticle includes at least one adsorbent functional group. The adsorbent functional group is selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups. The adsorbent catalytic nanoparticle also includes at least one catalytic material.

In various embodiments, the present invention provides a method including combining at least one adsorbent catalytic nanoparticle with at least one first molecule. The combining provides a mixture. The adsorbent catalytic nanoparticle includes at least one adsorbent functional group, wherein the at least one first molecule is selectively adsorbed by the adsorbent functional group. The adsorbent functional group is selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups. The adsorbent catalytic nanoparticle also includes at least one catalytic material.

In various embodiments, the present invention provides a method including combining at least one adsorbent catalytic nanoparticle with a fatty acid. The combining provides a mixture. The adsorbent catalytic nanoparticle includes at least one adsorbent functional group. The adsorbent functional group is selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups. The adsorbent catalytic nanoparticle also includes at least one catalytic material. The method includes combining the mixture with hydrogen gas so that the catalytic material at least one of cracks, decarboxylates, and hydrodeoxygenates at least some of the fatty acid.

In various embodiments, the present invention provides a method that includes combining at least one adsorbent catalytic nanoparticle with a solution. The solution includes a fatty acid and at least one of a fatty acid ester and a triglyceride. The combining provides a mixture. The adsorbent catalytic nanoparticle includes at least one adsorbent functional group. The adsorbent functional group is selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups. The adsorbent catalytic nanoparticle also includes at least one catalytic material. The method further includes separating the adsorbent catalytic nanoparticle having the first molecule adsorbed thereto from the mixture. The method further includes combining the separated adsorbent catalytic nanoparticle with hydrogen gas under conditions so that the catalytic material in the adsorbent catalytic nanoparticle catalyzes a chemical transformation of the fatty acid including at least one of cracking, decarboxylation, and hydrodeoxygenation.

Various embodiments of the present invention provide advantages over other mesoporous silica nanoparticles and methods of using the same, including some advantages that are unexpected. In various examples, the combination of the ability to not only separate particular substances from a mixture but also to catalyze the chemical transformation of those substances is unique and advantageous. In some embodiments, the proximity of the adsorbent functional groups and the catalytic material in the adsorbent catalytic nanoparticles yields desirable or advantageous and unexpected properties.

For example, the combination of adsorbent functional groups on the adsorbent catalytic nanoparticle and catalytic materials therein can cause molecules that are adsorbed by the adsorbent groups to be subjected to the catalytic material differently than molecules that are not adsorbed by the adsorbent groups. In some embodiments, the adsorbent functional groups can selectively adsorb a certain molecule or class of molecule from a mixture of molecules; thus, in various examples, the adsorbent catalytic nanoparticles can selectively expose certain molecules or classes of molecules to the catalytic material, thereby selectively causing a chemical transformation catalyzed by the catalytic material or influencing the selectivity thereof.

In some embodiments, the selectivity of a particular catalyst toward various chemical reactions of a molecule adsorbable by the adsorbant groups can be different when the molecule is adsorbed to an adsorbent group on the nanoparticle, versus when the molecule is not adsorbed to an adsorbant group on the nanoparticle. Thus, in various embodiments, the selectivity of the chemical reactions of a first molecule catalyzed by the catalytic material can be advantageously modulated by allowing the adsorbent groups to adsorb the first molecule prior to subjecting the first molecule and the adsorbent catalytic nanoparticle to conditions so that the catalytic material catalyzes a chemical transformation of the first molecule.

In some examples, by allowing adsorbent catalytic nanoparticles including a hydrotreatment catalyst to first adsorb a free fatty acid from a mixture, and then subjecting the nanoparticles with the adsorbed free fatty acid to conditions effective for the catalytic material to catalyze hydrotreatment, the products formed can advantageously and unexpectedly have a higher C:O ratio than can be achieved when the free fatty acid is hydrotreated using the catalytic material but with the catalytic material not having selectively adsorbant groups proximate thereto. In some examples, by allowing adsorbent catalytic nanoparticles including a hydrotreatment catalyst to first adsorb a free fatty acid from a mixture, and then subjecting the adsorbent catalytic nanoparticle with the adsorbed free fatty acid to conditions so that the catalytic material catalyzes hydrotreatment, the selectivity of the hydrotreatment toward hydrodeoxygenation can be higher as compared to the cracking and decarboxylation than can be achieved when the free fatty acid is hydrotreated using the catalytic material but not having selectively adsorbant groups proximate thereto, thereby yielding and increased average hydrocarbon length of the resulting product mixture; thus, various embodiments produce hydrocarbon mixtures having higher C:O ratios, higher cetane numbers, with less need for further processing, and/or are formed with less environmentally damaging release of $CO_2$.

In the manufacture of biodiesel, free fatty acids in the feedstock can form compounds by combining with certain catalytic materials, such as basic transesterification catalysts, to form soaps and consuming catalyst, thus reducing the efficiency of the process. In certain embodiments, the adsorbent catalytic nanoparticle can be used to efficiently remove fatty acids from a biodiesel feedstock, and subsequently to conveniently chemically hydrotreat the removed fatty acids, forming hydrocarbon mixtures that can be useful as fuel having better qualities than hydrotreated fatty acids produced by other methods, such as higher C:O ratio, and lower cost. The method of production can have less complexity and less energy use, and allow for the use of cheaper starting materials, such as for bio-diesel production. In certain embodiments, the adsorbent catalytic nanoparticle can be reused multiple times for separation of one or more materials from a mixture and subsequent catalytic conversion of the materials.

BRIEF DESCRIPTION OF THE FIGURES

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in FIG. 1a illustrates BET isotherms of $Ni_2P$-MSN, Ni-MSN, AP-Ni-MSN-0.5, and AP-Ni-MSN-2, in accordance with various embodiments.

DETAILED DESCRIPTION OF THE INVENTION

Figure 1A:
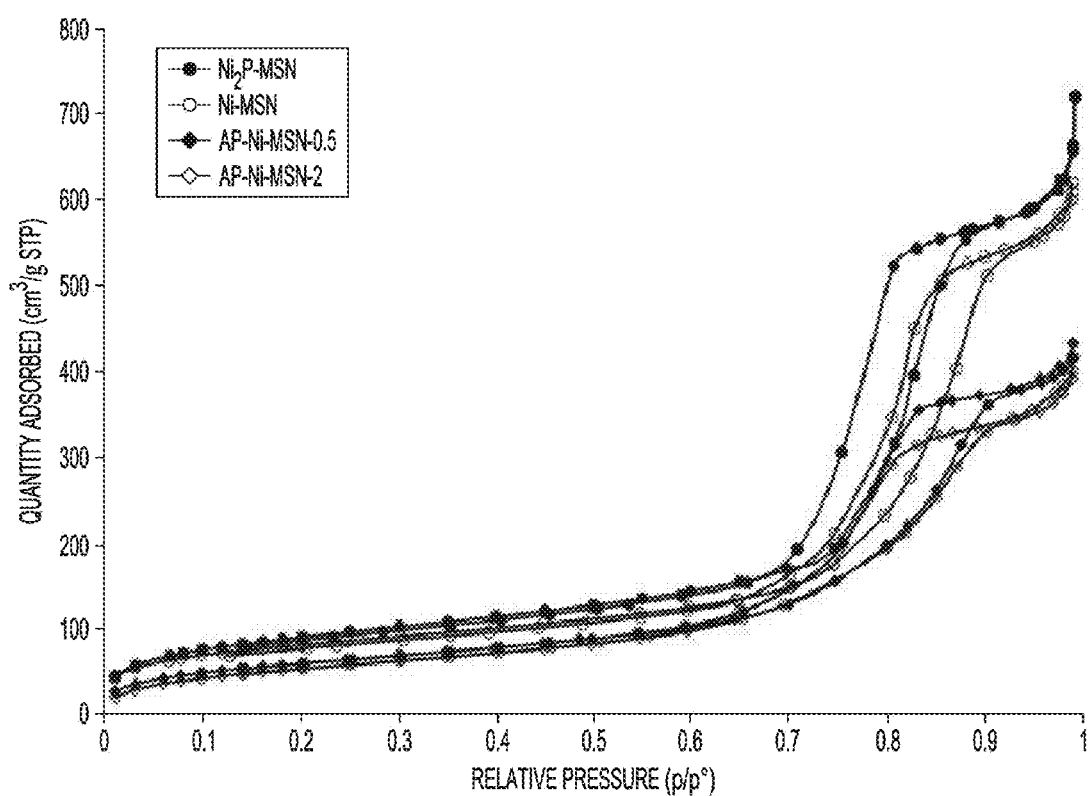
FIG. 1b illustrates X-ray diffraction patterns for Ni-MSN and $Ni_2P$-MSN, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "alkyl" as used herein refers to straight chain and branched alkyl groups and cycloalkyl groups having from 1 to 50 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "amine" as used herein refers to primary, secondary, and tertiary amines having, e.g., the formula N(group)$_3$ wherein each group can independently be H or non-H, such as alkyl, aryl, and the like. Amines include but are not limited to R—NH$_2$, for example, alkylamines, arylamines, alkylarylamines; R$_2$NH wherein each R is independently selected, such as dialkylamines, diarylamines, aralkylamines, heterocyclylamines and the like; and R$_3$N wherein each R is independently selected, such as trialkylamines, dialkylarylamines, alkyldiarylamines, triarylamines, and the like. The term "amine" also includes ammonium ions as used herein. An amino group is an amine substituent.

The terms "halo" or "halogen" or "halide", as used herein, by themselves or as part of another substituent mean, unless otherwise stated, a fluorine, chlorine, bromine, or iodine atom, preferably, fluorine, chlorine, or bromine.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "solvent" as used herein refers to a liquid that can dissolve a solid, liquid, or gas. Nonlimiting examples of solvents are silicones, organic compounds, water, alcohols, ionic liquids, and supercritical fluids.

The term "silica" as used herein refers to silicon dioxide (SiO$_2$) of any particle size, shape, particle size distribution, shape distribution and surface functionality, including chemically treated silicas. It can also refer to a polysiloxane that includes a silicon and oxygen atom network, including at least in part a silicon-oxygen-silicon-containing (silicon atom bonded to oxygen atom bonded to silicon atom) network, wherein the compound can be a polymer of any length or degree of branching. In various embodiments, the network can terminate with an Si=O group, or an Si—OH group. The silica gel or matrix can include polysiloxanes in 30%, 50%, 80%, 90%, 95%, 99%, 99.5%, 99.9%, or in any suitable percent composition (wt %).

The term "contacting" as used herein refers to the act of touching, making contact, or of bringing to immediate or close proximity, including at the molecular level, for example, to bring about a chemical reaction or physical change.

The term "adsorb" or "adsorption" as used herein refers to the binding of a molecule to an adsorbent group on a nanoparticle, wherein the molecule is reversibly or irreversibly bound to the particle. The binding can occur on the outer surface of the particle, including outer surfaces that are within the outer periphery of the particle, including the insides of pores that may be present in the nanoparticle.

The term "algae" as used herein refers to the paraphyletic group of simple, typically autotrophic, photosynthetic organisms, ranging from unicellular (e.g., green algae) to multicellular forms. Suitable algae genera can include *Botryococcus, Chlamydomas, Chlorella, Crypthecodinium, Cyclotella, Cylindrotheca, Dunaliella, Haematococcus, Isochrysis, Monallanthus, Monoraphidium, Nannochloris, Nannochloropsis, Neochloris, Nitzschia, Phaeodactylum, Schizochytrium, Spirulina, Stichococcus, Synechocystis, Tagetes*, and *Tetraselmis*. Specific species can include, for example, *Botryococcus braunii, Chlamydomas perigranulata, Chlorella emorsonii, Chlorella minutissima, Chlorella sorokiniana, Chlorella vulgaris, Crypthecodinium Cohnii, Cyclotella cryptica, Dunaliella Bardawil, Dunaliella sauna, Dunaliella primolecta, Haematococcus pluvialis, Isochrysis*

*galbana, Monallanthus sauna, Neochloris oleoabundans, Nitzschia closterium, Phaeodactylum tricornutum, Spirulina platensis, Tagetes erecta, Tagetes patula, Tetraselmis suecica,* or *Tetraselmis suecica.* Algea can include any suitable form of algae, including genetically modified algae, e.g., transgenic microalgae, are well known in the art. See, for example, Leon-Banares et al., *Trends in Biotechnology,* 22 (2004) 45-52.

The term "microalgae" as used herein refers to microscopic algae, typically found in freshwater and marine systems, often referred to as microphytes.

As used herein, the term "sequestering" or "sequestration" of a molecule, such as of a fatty acid from a mixture, refers to the process of concentrating a fatty acid. The concentration can occur by, for example, absorbing and/or adsorbing the fatty acid onto or into a nanoparticle. The adsorbing or adsorbing can include binding to the surface of the nanoparticle, such as by electrostatic associations, and the like.

The term "nanoparticles" as used herein refers to particles with an average diameter less than about 750 nm. In some embodiments, the particles can be less than about 500 nm, or less than about 300 nm, or approximately 50-200 nm. In some embodiments, nanoparticles can be approximately 75-100 nm in diameter.

The term "mesoporous" as used herein refers to containing pores wherein the pores have a diameter of between about 0.5 nm and about 200 nm, or between about 1 nm and about 100 nm, or between about 2 nm and about 50 nm.

The term "room temperature" as used herein refers to a temperature of about 15° C. to 28° C.

The term "hydrotreatment" as used herein is used to refer to a catalytic process performed in the presence of hydrogen that includes reductive chemical reactions, such as, for example, reduction of unsaturated bonds and reduction of carbon to lesser oxidation states via removal of bonds to oxygen or other heteroatoms, including, for example, carboxylate reduction, carboxylate decarboxylation, carboxylate decarbonylation, alkene reduction, reduction of conjugated or aromatic unsaturated bonds, reduction of any carbon-oxygen bond including, for example, conversion of glycerine to propane, or other reactions including carbon-carbon bond cracking and cycloparaffin formation via cyclization, or cycloparaffin formation via cyclization followed by hydrogenation/saturation of conjugated or nonconjugated C—C bonds, or aromatization. For example, hydrotreatment can include a catalytic process whereby oxygen is removed from organic compounds, for example as water (hydrodeoxygenation); sulfur from organic sulfur compounds, for example as dihydrogen sulfide (hydrodesulfurization); nitrogen from organic nitrogen compounds, for example as ammonia (hydrodenitrogenation); and halogens from organic compounds, for example, as chlorine from organic chloride compounds as hydrochloric acid (hydro dechlorination).

The term "fatty acid" as used herein refers to a carboxylic acid having a long-chain aliphatic hydrocarbon tail, e.g., R—C(O)OH where R is the aliphatic hydrocarbon tail, which can be saturated or unsaturated, and straight-chain, branched, or cyclic. Fatty acids can include short-chain fatty acids, having aliphatic tails of fewer than about 6 carbons, medium-chain fatty acids, having aliphatic tails of about 6-12 carbon atoms, long-chain fatty acids, having aliphatic tails of about 13-21 carbon atoms, and very long chain fatty acids, having aliphatic tails of greater than about 22 carbons. Fatty acids can include any suitable number of carbon atoms, such as about 1 to 50 carbon atoms. Fatty acid esters are esters of fatty acids. A free fatty acid is a fatty acid where in the acid group is a —C(O)OH group and is not a salt or an ester of the carboxylic acid group.

The term "triglyceride" as used herein refers to a fatty acid ester of glycerol.

Adsorbent Catalytic Nanoparticle

Various embodiments of the present invention provide an adsorbent catalytic nanoparticle, or a plurality of adsorbent catalytic nanoparticles. The adsorbent catalytic nanoparticle includes at least one adsorbent functional group bound to a mesoporous silica nanoparticle. The adsorbent catalytic nanoparticle also includes at least one catalytic material, which can be at least one of on the outside of the mesoporous silica nanoparticle and within the pores of the mesoporous silica nanoparticle. The adsorbent functional material can adsorb particular molecules that can be catalyzed by the catalytic material.

In some examples, the adsorbent catalytic nanoparticle can catalyze particular reactions of certain materials at a higher or lower rate than a corresponding mesoporous nanoparticle including the catalytic material but not having the adsorbent functional groups bound thereto, or at a higher or lower rate than the catalytic material free of the mesoporous silica nanoparticle and without the proximate adsorbent functional groups. For example, in some embodiments, the adsorbent catalytic nanoparticle can catalyze the decarboxylation and hydrodeoxygenation of a free fatty acid at a higher rate than a corresponding mesoporous nanoparticle including the catalytic material but not having the adsorbent functional group bound thereto. In some examples, the adsorbent catalytic nanoparticle can catalyze cracking of a free fatty acid at a lower rate than a corresponding mesoporous nanoparticle including the catalytic material but not having the adsorbent functional group.

In some embodiments, the percent selectivity of the adsorbent catalytic nanoparticle toward catalyzation of cracking of a free fatty acid is about 5-50%, 10-30%, or about 15-25% of the selectivity toward catalyzation of cracking of the free fatty acid of a corresponding mesoporous nanoparticle including the catalytic material but not having the adsorbent functional group bound thereto, or of the catalytic material free of nanoparticles. The percent selectivity of the adsorbent catalytic nanoparticle toward catalyzation of decarboxylation of a free fatty acid can be about 50-600%, 200-400%, or about 250-350% of the selectivity toward catalyzation of decarboxylation of the free fatty acid of a corresponding mesoporous nanoparticle including the catalytic material but not having the adsorbent functional group bound thereto, or of the catalytic material free of nanoparticles. The percent selectivity of the adsorbent catalytic nanoparticle toward catalyzation of hydrodeoxygenation of a free fatty acid can be about 50-1000%, 100-800%, 200-600%, 200-400%, or about 400-600% of the selectivity toward catalyzation of hydrodeoxygenation of the free fatty acid of a corresponding mesoporous nanoparticle including the catalytic material but not having the adsorbent functional group bound thereto. In this paragraph, percent selectivity is defined such that if the percent selectivity of cracking, decarboxylation, and hydrodeoxygenation is added, the sum is 100%.

The mesoporous silica nanoparticle is any suitable mesoporous silica nanoparticle, as is known to one of skill in the art. The mesoporous silica nanoparticle includes repeating —O—Si(R)$_2$— units, which form a silica matrix. The R group can independently designate any suitable substituent, including for example, siloxy, alkoxy, halo, or alkyl, wherein alkoxy or alkyl can be for example $C_1$-$C_{20}$ branched or straight chain. The repeating —O—Si(R)$_2$— units can be bound to any other suitable unit in the matrix. For example, an —O—Si(R)$_2$— unit can be bound directly to another silicon atoms, forming an —O—Si(R)$_2$—O— unit. In another example, an —O—Si(R)$_2$— unit can be bound to an alkoxy group, which can in turn be bound to any suitable substituent, such as a silicon atom-containing substituent, such as another —O—Si(R)$_2$— unit for example.

As an initial step in the preparation the adsorbent catalytic nanoparticles, mesoporous silica nanoparticles (MSNs) can be prepared. MSNs and their preparation are described in, for example, U.S. Patent Application Publication Nos. 2006/0154069 (Lin et al.), 2006/0018966 (Lin et al.), and Linton et al., *Chem. Mater.* 2008, 20, 2878-2880. Any suitable procedure can be used to generate the mesoporous silica nanoparticle. In some examples, a mesoporous silica nanoparticle can be made by condensing an alkoxysilane. In some examples, the alkoxysilane can be tetramethylortho silicate (TMOS), tetraethylortho silicate (TEOS), tetrakis(2-hydroxyethyl)ortho silicate (THEOS), methyldiethoxysilane (MDES), 3-(glycidoxypropyl)triethoxysilane (GPTMS), 3-(trimethyoxysilyl)propylacrylate (TMSPA), N-(3-triethoxysilylpropyl)pyrrole (TESPP), vinyltriethyoxysilane (VTES), methacryloxypropyltriethoxysilane (TESPM), diglycerylsilane (DGS), methyltriethoxysilane (MTMOS), trimethylmethoxysilane (TMMS), ethyltriethoxysilane (TEES), n-propyltriethoxysilane (TEPS), n-butyltriethyoxysilane (TEBS), 3-aminopropyltriethoxysilane (APTS), 2-(2,4-dinitrophenylamino)propyltriethoxysilane, mercaptopropyltriethoxysilane (TEPMS), 2-(3-aminoethylamino) propyltriethoxysilane, isocyanatopropyltriethoxysilane, hydroxyl-terminated polydimethylsiloxane, triethoxysilyl-terminated polydimethylsiloxane, methyltriethoxysilane (MTES), or triethoxysilyl-terminated poly(oxypropylene).

In some embodiments, acid or base treatment can allow hydrolysis of the alkoxysilane to give a reactive silanol, which can then react with other alkoxysilanes or silanols (e.g., to form —Si(R)$_2$—O—Si(R)$_2$— units) or with other reactive groups. In some embodiments, a reactive silanol can be provided by treatment of silica (e.g., SiO$_2$) with acid or base. Hydroxyl groups (e.g., R'—OH, wherein R' is any suitable substituent of suitable valancy, e.g., monovalent or divalent) from other compounds can condense with alkoxysilanes or silanols to give substituted silicones (e.g., —Si(R)$_2$—O—R'). Any suitable compound (e.g., silicon-containing or non-silicon containing) having any suitable number of hydroxyl or alkoxy groups (e.g., 1, 2, 3, 4, or more) can participate in the condensation, such that a wide variety of structures are possible for the mesoporous silica nanoparticle. For example, polyols can condense with multiple alkoxysilanes or silanols to give cross-linking of silicon atoms, e.g., HO—R'—OH can give —Si(R)$_2$—O—R'—O—Si(R)$_2$— units. Examples of suitable polyols can include any polyol that includes C$_{1-10}$ repeating alkylene oxide units, including polyols with more than one different C$_{1-10}$ repeating unit (e.g., ethylene oxide units such as in polyethylene glycol, propylene oxide units such as in propylene glycol, or a combination thereof such as in a copolymer of ethylene and propylene glycol), wherein the polyol can have any suitable chain length or molecular weight. As conventionally prepared, MSNs are spherical, but they can also been prepared under conditions that yield other shapes such as rods.

In some examples, the mesoporous silica nanoparticle and the corresponding adsorbent catalytic nanoparticle can be magnetic. Magnetism exhibited by the nanoparticle can be any kind of magnetism that allows the particle to be drawn in a particular direction by the effect of a magnetic field. The magnetism can include diamagnetism, paramagnetism, ferromagnetism, antiferromagnetism, ferrimagnetism, and superparamagnetism. The property of magnetism can result from iron oxide being included in or on the nanoparticle. The iron oxide can be any iron oxide known to one of skill in the art that can give magnetic properties to a nanoparticle, where in some embodiments the magnetic properties occur after further processing. Further processing can include reduction or oxidation of the iron oxide after inclusion in a nanoparticle. The iron oxide is at least one selected from Fe$_3$O$_4$ and Fe$_2$O$_3$.

The mesoporous silica nanoparticle can be transformed into a magnetic mesoporous nanoparticle via the addition of a magnetic iron oxide material. The iron oxide can be added by contacting the mesoporous silica nanoparticle with an iron precursor, optionally followed by a reduction or oxidation step. Thus, the adsorbent catalytic nanoparticle can include a reaction product of a mesoporous silica nanoparticle and an iron precursor.

The mesoporous silica nanoparticle can be contacted with an iron precursor, followed by an optional reduction or oxidation step, to give a magnetic mesoporous nanoparticle. The iron precursor can be any suitable iron precursor. For example, the iron precursor can be Fe(NO$_3$)$_3$, including Fe(NO$_3$)$_3$.9H$_2$O. Other examples include (NH$_4$)$_2$Fe(SO$_4$)$_2$, NH$_4$Fe(SO$_4$)$_2$, FeO, Fe$_3$O$_4$, Fe$_2$O$_3$, FeOCl, FeS, Fe(OAc)$_2$, FeX$_2$ or FeX$_3$ wherein X is independently chloro, bromo, or fluoro, Fe$_3$(PO$_4$)$_2$, FeSO$_4$, FeTiO$_3$, Fe(NO$_3$)$_3$, and the like, or any hydrate thereof. The reduction or oxidation is an optional step; in some embodiments, a reduction or oxidation is performed, while in other embodiments, a reduction or oxidation is not performed. The reduction or oxidation can be performed via any suitable means. In some examples, the reduction can be performed via application of H$_2$ gas. In some examples, the H$_2$ can be applied with heating.

In some embodiments, the mesoporous silica nanoparticle and the adsorbent catalytic nanoparticle can have a diameter of approximately 50 nm-1200 nm, or about 300-600 nm. The mesoporous silica nanoparticle and the adsorbent catalytic nanoparticle can have a surface area of approximately 100 m$^2$/g-1000 m$^2$/g, 200 m$^2$/g-500 m$^2$/g, or about 150 m$^2$/g-375 m$^2$/g. The mesoporous silica nanoparticle and the adsorbent catalytic nanoparticle can have a pore size of approximately 0.01 nm-100 nm, 1 nm-20 nm, or about 5 nm-15 nm. In some examples, the average pore volume of the mesoporous silica nanoparticle and the adsorbent catalytic nanoparticle can be about 0.001 cm$^3$/g to about 100 cm$^3$/g, 0.1 cm$^3$/g-6 cm$^3$/g, 0.25 cm$^3$/g-3 cm$^3$/g, or about 0.5 cm$^3$/g-1.5 cm$^3$/g. In some embodiment, the pores are hexagonally arranged. In some examples, the silicon oxide matrix of the silica nanoparticle can have hexagonal symmetry.

Adsorbent Groups

The adsorbent catalytic nanoparticle includes one or more adsorbent functional groups bound to the outer surface of a mesoporous silica nanoparticle. The adsorbent groups can be present inside none, some, or all of the pores of the nanoparticle, and can be present or not present on the remainder of the surface of the nanoparticle. Any suitable number and density of adsorbent functional groups can be on the mesoporous silica nanoparticle. For example, 0.001 mmol-1000 mmol, 0.01 mmol-50 mmol, or about 0.1 mmol-15 mmol of adsorbent functional groups can be on the nanoparticle per gram of the mesoporous silica nanoparticle.

The adsorbent functional group includes at least one selected from an amino(C$_1$-C$_{20}$)alkyl group or a salt thereof wherein the C$_1$-C$_{20}$ alkyl groups are independently optionally interrupted by one or two —NH— groups, a $(C_1-C_{20})$ alkyl carboxylic acid group or a salt thereof, a $(C_1-C_{20})$alkyl sulfonic acid group or a salt thereof, and a perfluoro$(C_1-C_{20})$alkyl group, wherein the alkyl unit of the aminoalkyl group, the alkyl carboxylic acid group, the alkyl sulfonic acid group, and the perfluoroalkyl group is covalently bound to a mesoporous silica nanoparticle. The adsorbent function group can include any suitable combination of aminoalkyl groups, alkyl carboxylic acid groups, the alkyl sulfonic acid groups, perfluoroalkyl groups, or salts thereof.

The adsorbent catalytic nanoparticle can include one or more amino$(C_1-C_{20})$alkyl groups or salts thereof with alkyl units covalently bound to the mesoporous silica nanoparticle, wherein the $C_1-C_{20}$ alkyl groups are optionally interrupted by one or two —NH— groups. In some embodiments, the $C_1-C_{20}$ alkyl groups are not interrupted by one or two —NH— groups. The amino$(C_1-C_{20})$alkyl groups on a given nanoparticle can all have approximately the same length $(C_1-C_{20})$alkyl group, or alternatively can have different lengths. Likewise, if an —NH— group interrupts an amino$(C_1-C_{20})$alkyl group, there can be the same number of —NH— groups interrupting each alkyl group, and there can be an —NH— group interrupting the alkyl group at the same location of the alkyl group, for all amino$(C_1-C_{20})$alkyl groups on a given nanoparticle. Also, —NH— groups can interrupt alkyl groups in varying numbers and location for all amino$(C_1-C_{20})$alkyl groups on a given nanoparticle. In one example, the adsorbent functional group can be an amino propyl group wherein the propyl unit is covalently bound to the mesoporous silica nanoparticle, e.g., to an oxygen or silicon atom.

The adsorbent functional group can be one or more $(C_1-C_{20})$alkyl carboxylic acid groups or salts thereof, with the $(C_1-C_{20})$alkyl units covalently bound to the mesoporous silica nanoparticle. For example, the $(C_1-C_{20})$alkyl carboxylic acid group can be —R—C(O)(OH), where R is $(C_1-C_{20})$alkyl, or $(C_1-C_{10})$alkyl, or $(C_2-C_6)$alkyl. The adsorbent functional group can be one or more $(C_1-C_{20})$alkyl sulfonic acid group or salts thereof, with alkyl units covalently bound to the mesoporous silica nanoparticle. For example, the $(C_1-C_{20})$alkyl sulfonic acid group can be —R—S(O)(O)(OH), where R is $(C_1-C_{20})$alkyl, or $(C_1-C_{10})$alkyl, or $(C_2-C_6)$alkyl. The adsorbent functional group can be one or more perfluoro$(C_1-C_{20})$alkyl groups, with the $(C_1-C_{20})$alkyl units covalently bound to the mesoporous silica nanoparticle, such as perfluoro$(C_1-C_{10})$alkyl, or perfluoro$(C_2-C_6)$alkyl. The $(C_1-C_{20})$alkyl units on a given nanoparticle in a given type of adsorbent group can all have substantially the same length, or can have different lengths.

The salt of the aminoalkyl group, the alkyl carboxylic acid group, and the alkyl sulfonic acid group can be any suitable salt. The adsorbent groups on a given adsorbent catalytic nanoparticle can be substantially all be salts, can be substantially all not salts (e.g., can be free acids or amines), and any suitable combination thereof. The salt can include any suitable counterion. Examples of suitable negative counterions (e.g., for forming a salt with an amine, an ammonium salt) can include a halide, such as fluoride, chloride, bromide, or iodide. In other examples, the negative counterion can be a nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate, an acid anion such as acetate or formate, or anions with negative charges greater than −1 (e.g., having in some embodiments one or more than one adsorbent functional group as counterion) such as oxide, sulfide, nitride, arsenate, phosphate, arsenite, hydrogen phosphate, sulfate, thio sulfate, sulfite, carbonate, chromate, dichromate, peroxide, or oxalate. Examples of suitable positive counterions (e.g., for forming a salt with a carboxylic acid or sulfonic acid) can include $Na^+$, $K^+$, $Cu^+$, $Li^+$, $Ag^+$, $Cs^+$, or anions with positive charges greater than 1 (e.g., for forming a salt with multiple acid groups) such as $Zn^{2+}$, $Fe^{2+}$, $Fe^{3+}$, $Ca^{2+}$, $Mg^{2+}$, $Zr^{2+}$, $Co^{2+}$, $Ni^{2+}$.

In some embodiments, the adsorbent catalytic nanoparticle can selectively adsorb one molecule or class or molecules over another molecule or class of molecules. For the adsorption to be selective, the selectivity can be less than exclusive. For example, if in a 1:1 mixture of compound or class of compounds A and compound or class of compounds B, a plurality of adsorbent catalytic nanoparticles adsorb 48% A and 52% B, the nanoparticles can be said to be selective toward adsorption of B. Also, if in a 1:1 mixture of A and B, a plurality of adsorbent catalytic nanoparticles adsorb 25% A and 75% B, the nanoparticles can be said to be selective toward adsorption of B. Also, if in a 1:1 mixture of A and B, a plurality of adsorbent catalytic nanoparticles adsorb 1% A and 99% B, the nanoparticles can be said to be selective toward adsorption of B. The adsorbent catalytic nanoparticles can selectively adsorb substantially all of compound or class of compounds A and adsorb substantially none of compound or class of compounds B. In any one of these examples of selectivity, one or more other compounds can be present, and similarly the adsorbent catalytic nanoparticles can be selective against adsorption of any one or more of the other compounds and selective towards adsorption of compound or class of compounds A or compound or class of compounds B. In various examples, the adsorbent catalytic nanoparticles can adsorb fatty acids at a higher rate than at least one of fatty acid esters and triglycerides.

Catalytic Material

The adsorbent catalytic nanoparticle can include one or more catalytic materials in, on, or both in and on the mesoporous silica nanoparticle. The catalytic material can be on the outer surface of the nanoparticle. The catalytic material can be present inside none, some, or all of the pores of the mesoporous silica nanoparticle, and can be present or not present on the remainder of the surface of the mesoporous silica nanoparticle. The catalytic material can be evenly distributed within the pores of the mesoporous silica nanoparticle. The catalytic material can have any suitable form. In some examples, the catalytic material can include at least one of crystalline catalytic material, catalytic nanoparticles, a coating of catalytic material, or a coating of catalytic nanoparticles. In various embodiments, the adsorbent catalytic nanoparticle can include about 1-30 wt %, 1-20 wt %, or about 5-15 wt % catalytic material. For example, the adsorbent catalytic nanoparticle can include about 5-15 wt % Ni, such as in the form of Ni or $Ni_2P$.

The catalytic material can be any suitable type of catalyst. In some examples, the catalytic material can be at least one of nickel, nickel phosphide (e.g., $Ni_2P$), iron, iron oxide (e.g., $Fe_3O_4$ or $Fe_2O_3$), rhodium, ruthenium, gold, cobalt, cobalt oxide, palladium, platinum, and molybdenum. In some examples, the catalytic material is a hydrotreatment catalyst. The catalytic material can catalyze at least one of cracking, decarboxylation, and hydrodeoxygenation. The catalyst can be any suitable hydrotreating catalyst. The hydrotreating catalyst can include one or more metals from IUPAC groups 6, 8, 9, and 10 of the periodic table of the elements. In some examples, the one or more metals can be selected from palladium (Pd), platinum (Pt), nickel (Ni), and combinations thereof. In embodiments, the catalyst is a nickel-molybdenum (NiMo) catalyst including nickel and molybdenum. In some embodiments, the catalyst is a cobalt-molybdenum (CoMo) catalyst. In embodiments, NiMo/Al$_2$O$_3$—SiO$_2$ or CoMo—Al$_2$O$_3$ catalyst is utilized. In some embodiments, a Ni catalyst is utilized. In some embodiments, a molybdenum catalyst is utilized. In some embodiments, a catalyst with any suitable proportion of Ni and Mo is utilized.

Method of Using an Adsorbent Catalytic Nanoparticle

Various embodiments of the present invention provide any suitable method of using the adsorbent group-functionalized mesoporous silica nanoparticle including the catalytic material. The method can include combining at least one adsorbent catalytic nanoparticle with at least one first molecule that is selectively adsorbed by the adsorbent functional group, to provide a mixture. In some examples, the first molecule is a free fatty acid. A single adsorbent catalytic nanoparticle can adsorb one or more than one first molecule. In some examples, each adsorbent catalytic nanoparticle can adsorb a quantity of the first molecules equal to about one to the quantity of adsorbent functional groups substituted on the mesoporous silica nanoparticle. Throughout the description of the nanoparticle and the method, where a first molecule is described, such as the selective adsorption, separation, and reaction thereof, a first family of molecules are also described and included as an embodiment of the present invention. For example, the first family can be fatty acids. Likewise, where a second molecule is described, a second family of molecules is likewise described, such at least one of fatty acid esters and triglycerides.

The method can include combining the mixture with as first reagent, under conditions so that the catalytic material in the adsorbent catalytic nanoparticle catalyzes a chemical transformation of the first molecule. For example, the first reagent can be hydrogen, and the catalytic material can be a hydrotreatment catalyst, such that the catalyzation of the chemical transformation of the first molecule is hydrotreatment of the first molecule.

Hydrotreating can include contacting the conversion component with a hydrotreatment catalyst and hydrogen gas. The contacting can be any suitable contacting. For example, the hydrotreatment catalyst and hydrogen gas can be contacted with the conversion component in a reactor. The hydrotreating can occur at any suitable temperature, pressure, and for any suitable time such that the hydrotreating generates suitable hydrotreated material for moving forward in the processing. The temperature can be about 150° to 1000° C., about 250° to 600° C., about 200° to 500° C., about 250° to 450° C., about 300° to 550° C., about 300° to 400° C., or about 340° to 530° C. Reactor pressures can be about 1 to 1000 bar, about 10 to 500 bar, about 10 to 300 bar, or about 100 to 150 bar. In some embodiments, reactor pressures can be about 25 to 250 bar, while in some embodiments, reactor pressures can be about 60 to 200 bar. The duration of the hydrotreatment can be any suitable duration, such as about 1 minute, 5 minutes, 10 minutes, 20 minutes, 30 minutes, 60 minutes, 4 hours, about 8 hours, or more.

In some examples, combining the adsorbent catalytic nanoparticle with the first molecule can include combining the adsorbent catalytic nanoparticle with a solution including the molecule that is selectively adsorbed by the adsorbent functional group, to provide the mixture. The solution can further include comprise at least one second molecule that is at least one of not adsorbed by the adsorbent functional group and adsorbed by the adsorbent functional group at a lower rate than the first molecule is adsorbed by the adsorbent functional group. In some embodiments, the solution can include a solvent. The first molecule can be any suitable mole percent of the mixture. For example, not including the solvent, the first molecule can be about 0.0001 mol % of the mixture, or about 0.001, 0.01, 0.1, 1, 2, 3, 4, 5, 10, 15, 20, 40, 60, 80, 90, 95, 96, 97, 98, 99, 99.9, 99.99, 99.999 mol % of the mixture. In some examples, the second molecule is at least one of a fatty acid ester and a triglyceride, such as at least one of a C$_{1-50}$ fatty acid C$_{1-50}$ ester and a triglyceride having C$_{1-50}$ fatty acid groups. In some embodiments, the first molecule is a free fatty acid such as a C$_{1-50}$ free fatty acid.

The adsorbent catalytic nanoparticles and the at least one compound can be exposed to one another at any relative concentration, and for any duration of time, sufficient to allow formation of at least some adsorbent catalytic nanoparticles having first molecules adsorbed thereon. For example, the duration of time can be about 1 minute, 5 minutes, 10 minutes, 20 minutes, 30 minutes, 60 minutes, 4 hours, about 8 hours, or more.

In various embodiments, the method can include separating the adsorbent catalytic nanoparticles from the mixture, including the adsorbent catalytic nanoparticles having the at least one first molecule adsorbed thereto, and optionally additionally including any adsorbent catalytic nanoparticle not having the first molecule adsorbed thereto. In some embodiments, the separated mixture can be at least one of used and sold as a feedstock for generating biodiesel. The method can include combining the separated adsorbent catalytic nanoparticle with a first reagent under conditions so that the catalytic material in the adsorbent catalytic nanoparticle catalyzes a chemical transformation of the first molecule. For example, the regent can include hydrogen gas and the conditions can be any suitable conditions described herein such as those described as suitable for hydrotreatment. In some embodiments, the method includes at least one of using and selling the product of the chemical transformation of the first molecule as a fuel, such as a transportation fuel such as gasoline or diesel.

In some embodiments, when the adsorbent group-functionalized mesoporous silica nanoparticles including catalytic material are magnetic, the magnetic property can be used to separate the adsorbent catalytic nanoparticles including the at least one first molecule adsorbed thereto, such as by using a magnetic field. The magnetic field can be generated in any effective method known to one of skill in the art, and can be of any strength sufficient to concentrate the adsorbed first molecules. The magnetic field can be generated by an electromagnet, a non-electromagnet, or a combination thereof. The magnetic field can originate from a source that is in contact with the media, or from a source that is outside the approximate boundaries of the media. The magnetic field can originate from multiple sources, and the multiple sources can be in different locations.

The exposure to the magnetic field is sufficient to concentrate the first molecule or family of molecules. Concentration refers to the amount of first molecules in a given volume of the media, and can refer to any degree of concentration. Concentration can include an at least 0.01%, 5%, 10%, 20%, 40%, 80%, 90%, 95%, 99% increase in the moles of the first molecules in a given volume of the media. Concentrating the first molecules can also include removing the adsorbed first molecules from the media, which corresponds to the given volume of the media approaching zero as the amount of the first molecules remains constant. Concentrating the first molecules can refer to the effect of the magnetic field on any number of adsorbent catalytic nanoparticles with adsorbed first molecules, including all of the nanoparticles, substantially all the nanoparticles, some of the nanoparticles, a few of the nanoparticles, or one of the nanoparticles with adsorbed first molecules. The adsorbent catalytic nanoparticles without adsorbed first molecules can be substantially equally affected by the applied magnetic field. The exposure to the magnetic field can be sufficient to move the nanoparticles towards the magnetic field. The exposure to the magnetic field can be sufficient to move the nanoparticles away from the magnetic field. The exposure can be sufficient to induce a magnetic field in each exposed nanoparticle. The exposure can be sufficient to cause the nanoparticles to move toward or away from a specific direction. The exposure can be sufficient to cause the nanoparticles to gather in a specific area. The remainder of the mixture can be transferred away from the first molecules, or the nanoparticles can be transferred away from the remaining mixture, such as by decanting, draining, centrifuging, siphoning, pumping, gravity, or a combination thereof.

EXAMPLES

The present invention can be better understood by reference to the following examples which are offered by way of illustration. The present invention is not limited to the examples given herein.

General.

Pluronic was provided by BASF. Tetramethyl orthosilicate (TMOS) was purchased from Sigma Aldrich. 3-Aminopropyl trimethoxysilane (APTMS) was purchased from Gelest. Nickel nitrate hexahydrate [$Ni(NO_3)_2 \cdot 6H_2O$] and ammonium phosphate [$(NH_4)_2HPO_4$] were purchased from Fisher Scientific.

Example 1

Synthesis of Mesoporous Silica Nanoparticles (MSN)

The nonionic surfactant Pluronic P104 (7.0 g) was added to HCl (273.0 g, 1.6 M). After stirring for 1 h at 56° C., tetramethylorthosilicate (TMOS, 10.64 g) was added and stirred for an additional 24 h. The resulting mixture was further post hydrothermally treated for 24 h at 150° C. in a high-pressure reactor. Upon cooling to room temperature, the white solid was collected by filtration, washed with copious amounts of methanol and dried in air. To remove the surfactant P104 by calcination, the MSN material was heated at a ramp rate of 1.5° C. min$^{-1}$ and maintained at 550° C. for 6 h.

Example 2

Synthesis of Nickel Nanoparticles in the Pores of MSN (Ni-MSN)

MSN was mixed with water and stirred at room temperature in order to rehydrate and regenerate the silanol groups, followed by filtration and drying. $Ni(NO_3)_2 \cdot 6H_2O$ (0.55 mmol, 0.16 g) was completely dissolved in water (0.48 mL). To this solution, the rehydrated MSN (0.4 g) was added and mixed. The solid mixture was calcined in air at a heating rate of 2° C. min$^{-1}$ to 500° C. and maintained at that temperature for 6 h followed by reduction at 450° C. for 5 hours in a constant flow of $H_2$ (0.5 mL/s).

Example 3

Synthesis of Nickel Phosphide Nanoparticles in the Pores of MSN Ni$_2$P-MSN)

$Ni(NO_3)_2 \cdot 6H_2O$ (0.55 mmol, 0.16 g) and $(NH_4)_2HPO_4$ were completely dissolved in water (0.48 mL). To this solution, the rehydrated MSN (0.4 g) was added and mixed. The solid mixture was calcined in air at a heating rate of 2° C. min$^{-1}$ to 500° C. and maintained at that temperature for 6 h followed by temperature programmed reduction (TPR) at 650° C.

Example 4

Synthesis of 3-aminopropyl trimethoxysilane functionalized Ni-MSN (AP-Ni-MSN)

Amine functionalized materials were prepared by grafting APTMS (0.5 mmol, 0.09 g for AP-Ni-MSN-0.5 and 2 mmol, 0.36 g for AP-Ni-MSN-2) to the surface of Ni-MSN (1 g) in refluxing toluene (100 mL) for 24 hours. The resulting solid was filtered, washed with methanol and dried under vacuum for 24 h.

Example 5

Characterization

Surface analysis of the catalyst was performed by nitrogen sorption isotherms in a Micromeritics Tristar surface area and porosity analyzer. The surface areas were calculated by the Brunauer-Emmett-Teller (BET) method and the pore size distribution were calculated by the Barrett-Joyner-Halenda (BJH) method. The small angle powder X-ray diffraction patterns were obtained with a Rigaku Ultima IV diffractometer using Cu target at 40 kV and 44 mA. Cu K$\beta$ was removed using a monochromator. For transmission electron microscopy measurements, an aliquot of the powder was sonicated in methanol for 15 min. A single drop of this suspension was placed on a lacey carbon coated copper TEM grid and dried in air. The TEM examination was completed on a Tecnai G2 F20 electron microscope operated at 200 kV. Fourier transform infrared (FT-IR) spectra were recorded on Nicolet Nexus 470. TPD measurements were performed in Autochem. Perkin Elmer ICP-MS was used to measure Ni loading and Agilent GC-MS was used to measure reaction products.

Example 6

General Procedure for One-Step Batch Reaction, Also Called Simultaneous Catalysis or Tandem Sequestration Catalysis All catalytic reactions were performed in a batch reactor (Parr Instrument). In a typical experiment, the catalyst (10 mg) and oleic acid solution in hexanes (1 mM, 10 mL) were added in the reactor. The reactor was purged with $H_2$ at ambient temperature and was finally pressurized by $H_2$ to 30 bar. The reaction was carried out at 290° C. for 6 h with constant stir rate. The reaction was allowed to cool to room temperature and the products were subjected to esterification in order to derivatize the remaining oleic acid to oleic acid methyl ester for analysis by GC-MS. In order to derivatize, the hexanes were removed under reduced pressure followed by the addition of HCl (1 M, 2 mL). The mixture was stirred for 1 h at 80° C. After cooling to room temperature, NaCl (1%, 1 mL) was added to the reaction mixture to increase the recovery of oleic acid methyl ester by solvent extraction. The ester of oleic acid was extracted with hexanes (3×3 mL) and was analyzed by GC-MS methyl nonadecanoate ($C_{19}$) as an internal standard.

Example 7

General Procedure for Integrated Batch Reaction, Also Called Sequential Sequestration-Catalysis In a typical two-step process, the catalyst (10 mg) was added to a test tube containing the oleic acid solution in hexanes (1 mM, 10 mL), mixed for 6 h and then the suspension was centrifuged. The amount sequestered was calculated by measuring the oleic acid remaining in the supernatant. In order to convert the sequestered oleic acid to liquid hydrocarbons, the catalyst remaining after centrifugation was mixed with 10 mL hexanes and the mixture was loaded to the reactor. After purging with $H_2$, the reaction mixture was kept at 290° C. and 450 psi for 6 h with constant stirring. The reaction was allowed to cool to room temperature and the liquid samples were analyzed by GC-MS using $C_{19}$ internal standard.

Example 8

Physiochemical Characterization and Activity of Ni-MSN and $Ni_2P$-MSN

Figure 1B:
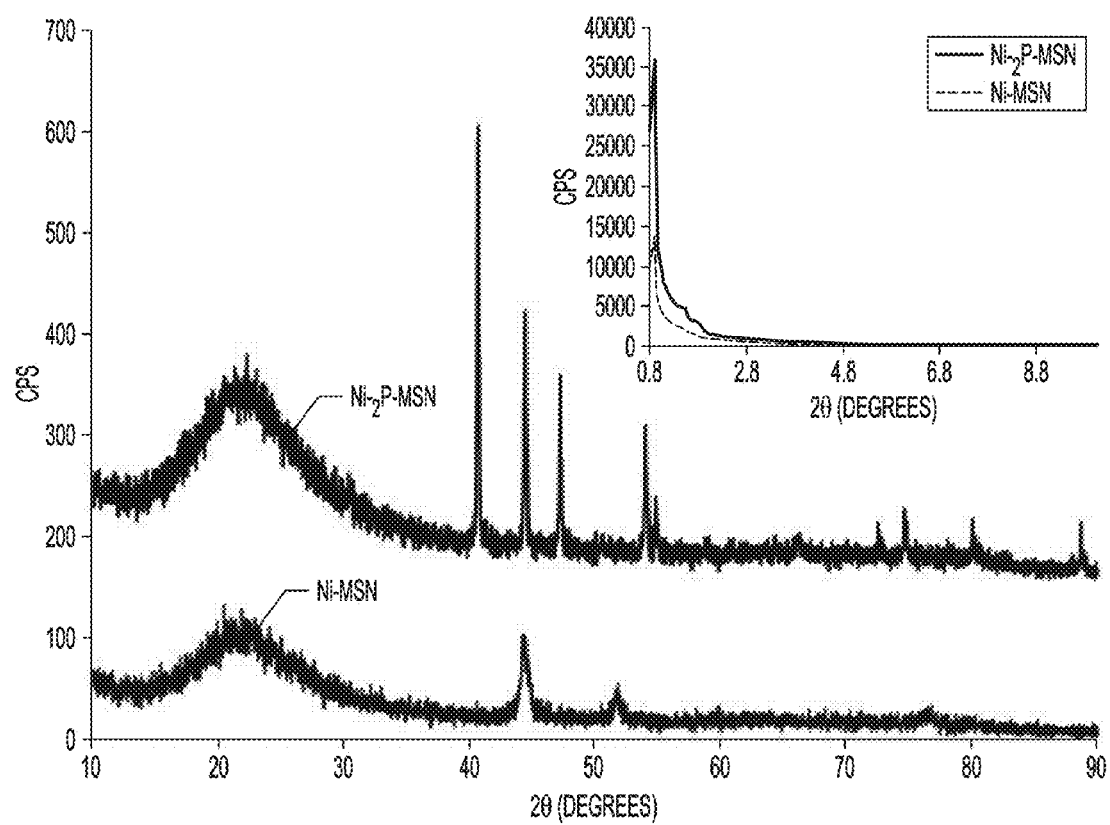
Figure 2A:
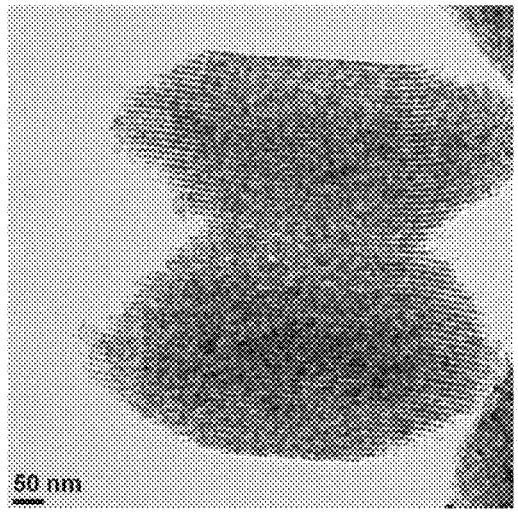
FIG. 2a illustrates a TEM image of Ni-MSN, in accordance with various embodiments.
Figure 2B:
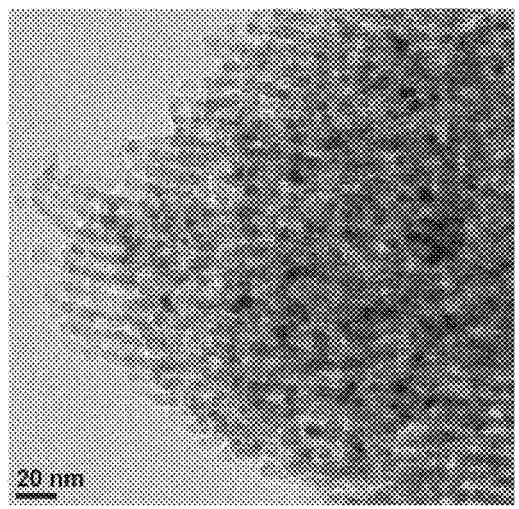
FIG. 2b illustrates a TEM image of Ni-MSN, in accordance with various embodiments.
Figure 2C:
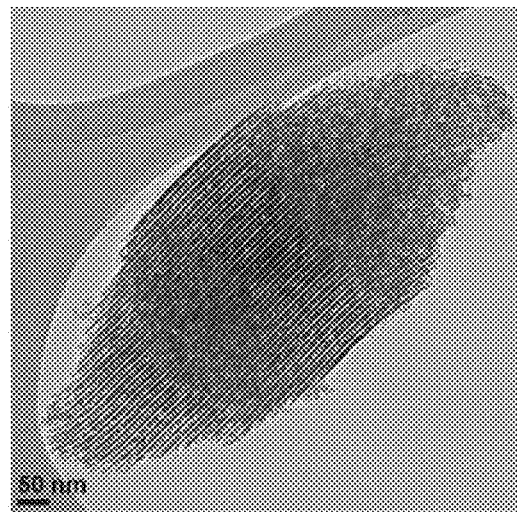
FIG. 2c illustrates a TEM image of $Ni_2P$-MSN, in accordance with various embodiments.

The textural properties of Ni-MSN and $Ni_2P$-MSN were obtained from nitrogen sorption analysis using BET and BJH calculations (FIG. 1a). FIG. 1a illustrates BET isotherms of $Ni_2P$-MSN, Ni-MSN, AP-Ni-MSN-0.5, and AP-Ni-MSN-2. Both materials possess type IV isotherms which is characteristic of mesoporosity. The values for all the structural parameters are summarized in Table 1. FIG. 1b shows the X-ray diffraction pattern for Ni-MSN and $Ni_2P$-MSN, with the inset showing low angle XRD patterns and the larger plot showing wide angle XRD patterns. The observed diffraction patterns with intense ($d_{100}$) peaks are characteristic of highly ordered two-dimensional (2D) hexagonal mesostructures with uniform channels. The presence of ($d_{110}$) and ($d_{200}$) in both materials indicates that the structural order is maintained and suggests that both Ni and $Ni_2P$ particles are evenly distributed inside the channels in the MSNs. The characteristic peaks of both Ni and $Ni_2P$ in high angle X-ray diffraction confirm the formation of crystalline metallic nickel and $Ni_2P$ phase (FIG. 1b) respectively. The homogeneous distribution of both Ni and $Ni_2P$ particles in the channels of MSN was further confirmed by TEM-EDX images shown in FIGS. 2a and 2c, showing Ni-MSN and $Ni_2P$-MSN, respectively. FIG. 2b shows a zoomed-in view of FIG. 2a, more clearly showing particles of Ni in the MSN. As summarized in Table 1, after the formation of Ni and $Ni_2P$ crystalline phase in the mesopores of MSN, both materials maintained similar structural properties. This provides evidence the difference in the active catalytic phase i.e. Ni and $Ni_2P$ may be responsible for the observed difference in catalytic activity.

TABLE 1

Summary of textural properties of catalysts.

| Sample | Surface area ($m^2/g$) | Pore Volume ($cm^3/g$) | Pore Size (nm) | Ni Loading (wt. %) | AP Loading (mmol/g) |
|---|---|---|---|---|---|
| Ni-MSN | 298 | 0.9 | 11 | 6.9 | 0 |
| $Ni_2P$-MSN | 317 | 1.0 | 11 | 5.2 | 0 |
| AP-Ni-MSN-0.5 | 227 | 0.6 | 9.1 | 6.6 | 0.5 |
| AP-Ni-MSN-2 | 209 | 0.6 | 8.9 | 6.5 | 2 |

As a reference reaction, the catalytic conversion of oleic acid was carried out at 290° C. and 30 bar $H_2$ for 6 hours in batch mode. Some of the possible reactions of the oleic acid reaction include cracking, decarboxylation, and hydrodeoxygenation (Scheme 1).

Scheme 1. Reaction products.

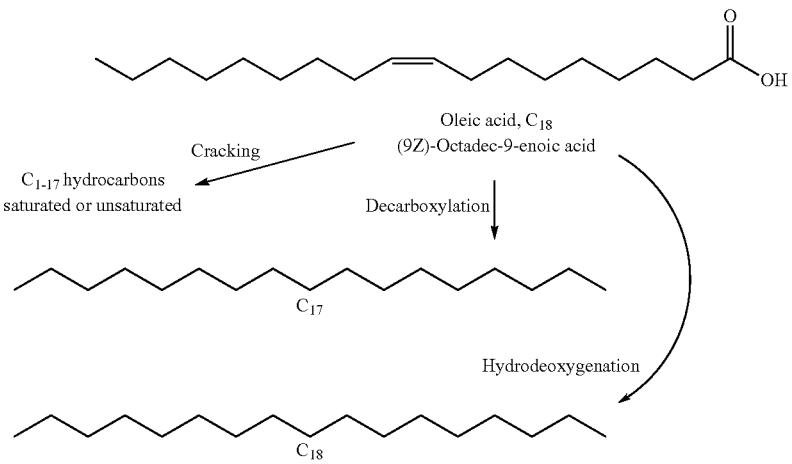

Figure 3:
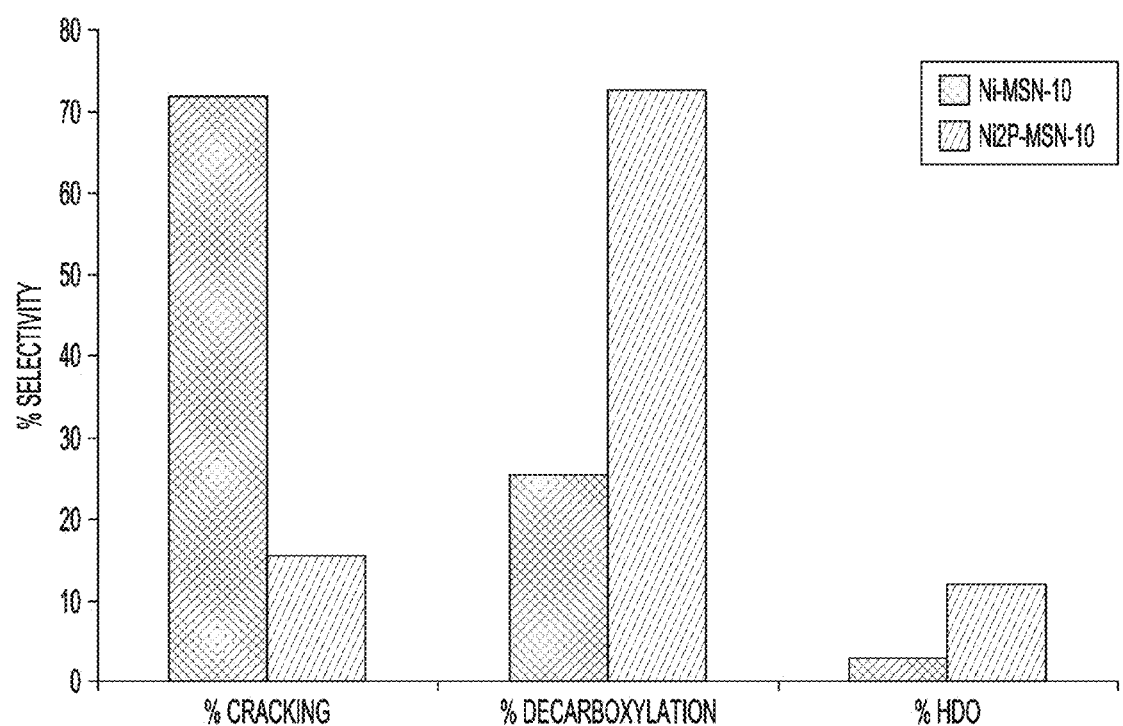
FIG. 3 illustrates the selectivities of Ni-MSN and $Ni_2P$-MSN catalyst for conversion of oleic acid, in accordance with various embodiments.

The observed selectivities while using Ni-MSN and $Ni_2P$-MSN catalyst for conversion of oleic acid are shown in FIG. 3. Ni-MSN led to selectivities of 72% cracking, 25% decarboxylation and 3% HDO while the selectivities of cracking decreased by approximately five fold to 15% and that of decarboxylation of oleic acid to heptadecane ($C_{17}$) increased almost by three fold to 73% with $Ni_2P$-MSN catalyst. In addition, the selectivity for hydrodeoxygenation of oleic acid to octadecane ($C_{18}$) increased by four fold to 12% using $Ni_2P$-MSN as a catalyst.

Example 9

Sequestration of Oleic Acid by Ni-MSN and AP-Ni-MSN

Figure 4A:
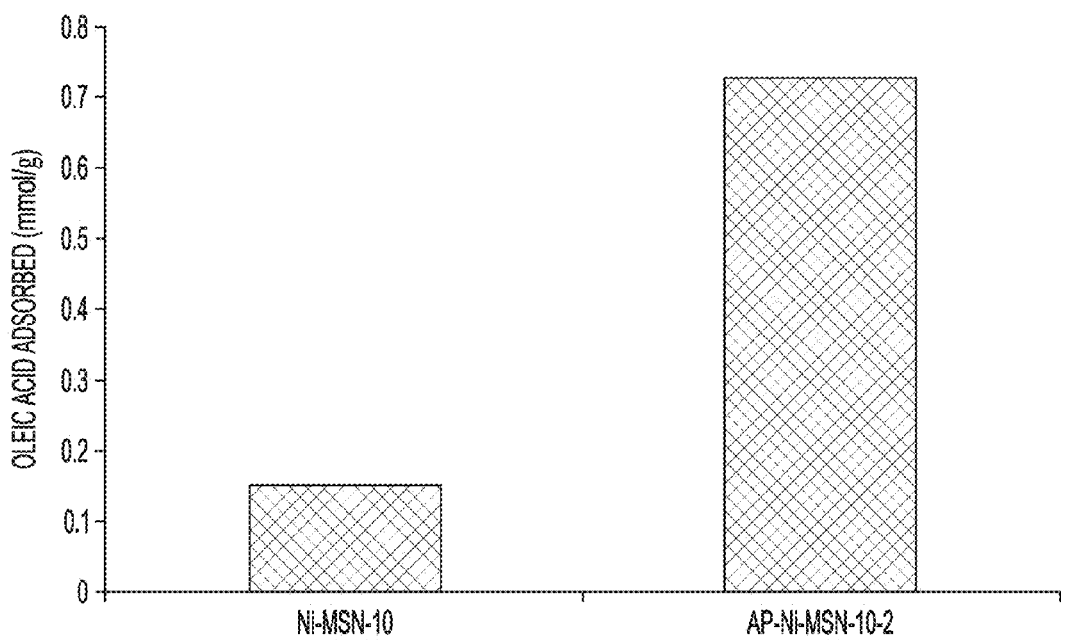
FIG. 4a illustrates a comparison of the sequestration of oleic acid using Ni-MSN-10 and AP-Ni-MSN-10-2, in accordance with various embodiments.

Free fatty acids can be sequestered using 3-aminopropyl trimethoxysilane functionalized MSN (AP-MSN). In order to increase the proximity and concentrate oleic acid near Ni particles in the channels of Ni-MSN, amino propyl group was functionalized on the surface of Ni-MSN to obtain AP-Ni-MSN-2 material. While the maintenance of pore structure was confirmed by nitrogen sorption analysis, as shown in FIG. 1a, a small decrease in pore volume (0.9 $cm^3/g$ to 0.6 $cm^3/g$) and pore size (11 nm to 8.9 nm) along with a drop in surface area (298 $m^2/g$ to 209 $m^2/g$) was observed after functionalization. Despite the loss in surface area, AP-Ni-MSN-2 sequestered 73% of available oleic acid (0.73 mmol oleic acid/g of material from a 1.0 mM oleic acid solution) compared to 15% (0.15 mmol oleic acid/g of material) by Ni-MSN, as shown in FIG. 4a.

Figure 4B:
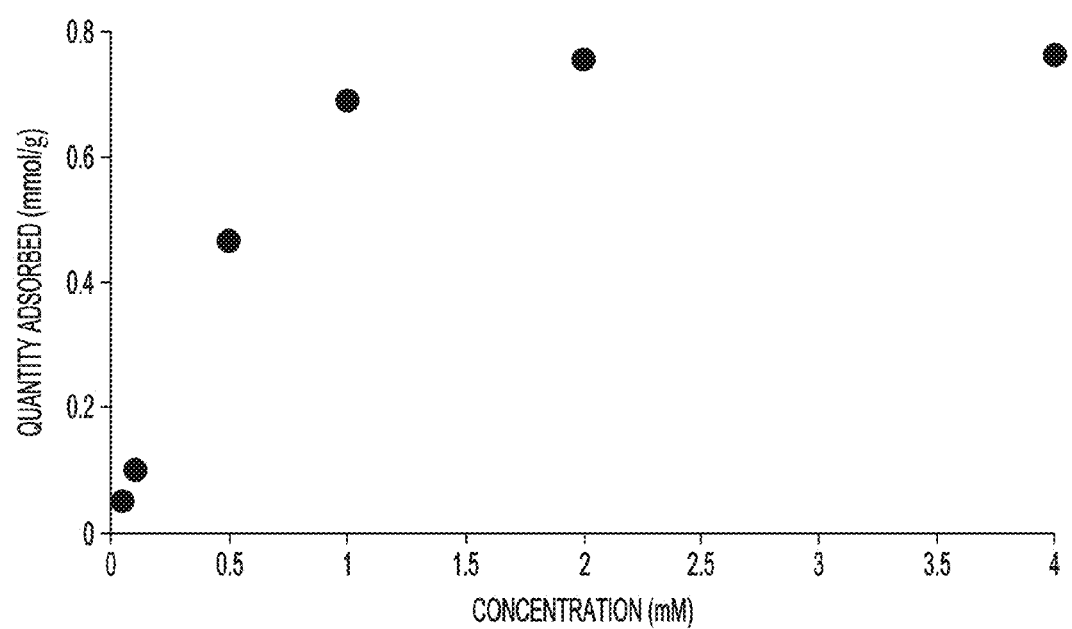
FIG. 4b illustrates the sequestration of oleic acid at various concentrations using AP-Ni-MSN-10-2, in accordance with various embodiments.
Figure 4C:
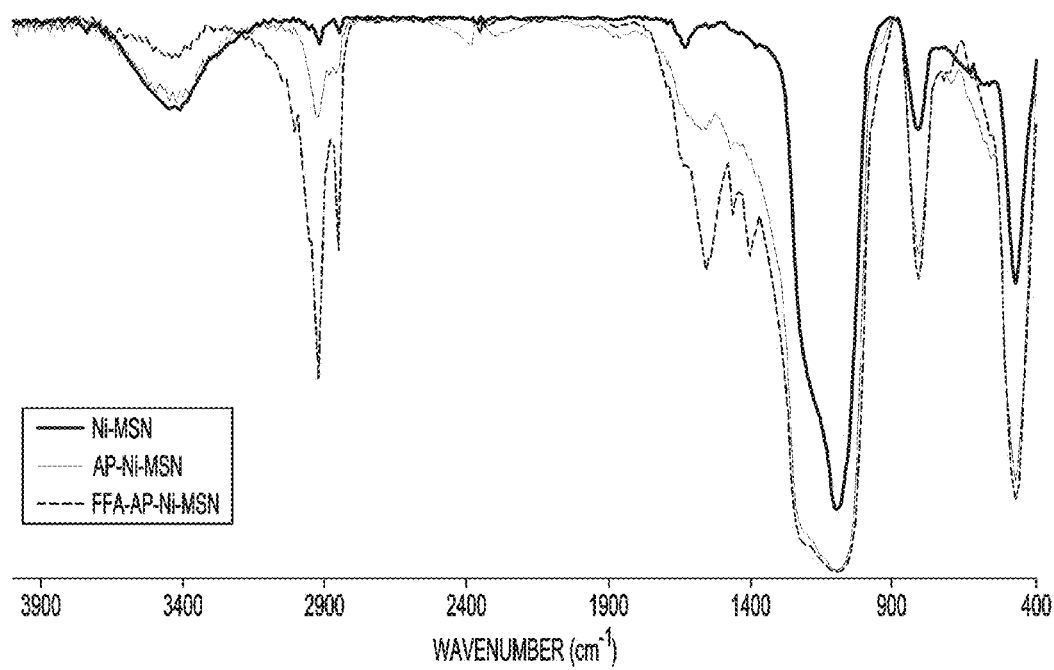
FIG. 4c illustrates the infrared spectra of Ni-MSN, AP-Ni-MSN, and oleic acid-adsorbed AP-Ni-MSN, in accordance with various embodiments.

To further examine the sequestration capacity, AP-Ni-MSN (10 mg) was mixed with the varying concentration of oleic acid for 6 h. The amount of oleic acid sequestered by AP-Ni-MSN sharply increased at lower concentrations and eventually plateaued at higher concentrations with maximum adsorption of 0.76 mmol oleic acid $g^{-1}$ of adsorbent (FIG. 4b). The sequestration of oleic acid by AP-Ni-MSN was confirmed by the presence of sharp C—H stretching bands at 2926 $cm^{-1}$ and 2850 $cm^{-1}$ as well as the two assymetrical and symmetrical carboxylate vibrations at 1558 $cm^{-1}$ and 1403 $cm^{-1}$ respectively (FIG. 4c). Whether the sequestration capacity of AP-Ni-MSN could impose a synergistic effect during catalysis by increasing the local concentration of oleic acid near the Ni catalytic site was examined in subsequent Examples.

Example 10

Effect of Amine Functionalization on Catalytic Activity

Figure 5:
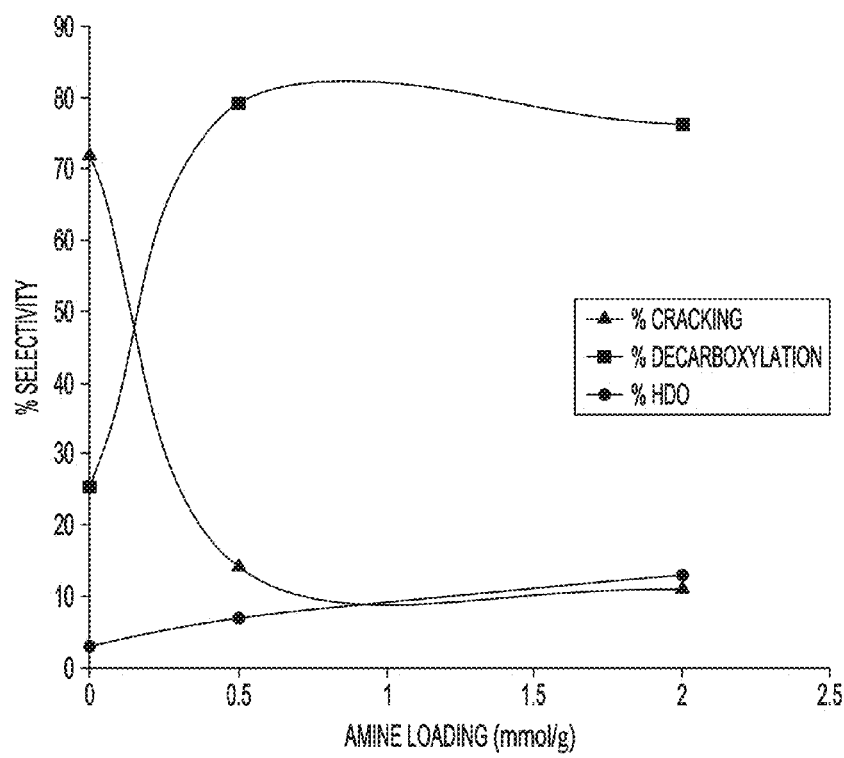
FIG. 5 illustrates the percent selectivity of Ni-MSN having various levels of amine loading toward various reactions, in accordance with various embodiments.
Figure 6:
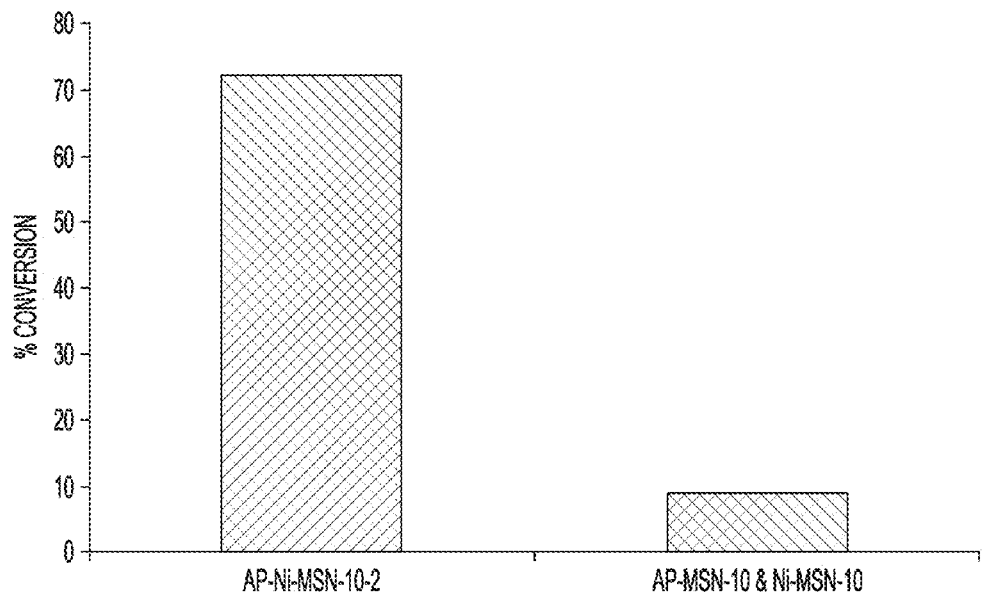
FIG. 6 illustrates the percent conversion of oleic acid when a mixture of AP-MSN and Ni-MSN was used, in accordance with various embodiments.

To explore the effect of amine functionalization on catalytic conversion of oleic acid, Ni-MSN with different loading of amino propyl group (0.5 mmol/g Ni-MSN and 2 mmol/g Ni-MSN) was synthesized. These two materials were denoted as AP-Ni-MSN-0.5 and AP-Ni-MSN-2 respectively and possessed similar textural properties as shown in Table 1 and FIG. 1. Functionalization of amine led to decrease in selectivity of cracking from 72% by Ni-MSN to 14% by AP-Ni-MSN-0.5 and increase in decarboxylation and HDO selectivity to 79% and 7% respectively, compared to Ni-MSN. Further decrease in O:C ratio of the product was obtained by increasing the loading of amino functional group on Ni-MSN i.e. the selectivity toward $C_{18}$ via HDO was two times more for AP-Ni-MSN-2 catalyst compared to AP-Ni-MSN-0.5, as shown in FIG. 5. These enhancements for simultaneous sequestration-catalysis is may be due to the proximity of an amino group and Ni catalytic site. The amino group can concentrate the oleic acid near the Ni sites for a synergistic catalytic effect. When the physical mixture of amine functionalized mesoporous silica nanoparticle (AP-MSN) and Ni-MSN was used as catalyst, only 9% of available oleic acid was converted to hydrocarbons (FIG. 6). This suggests that the kinetics of oleic acid sequestration by AP-MSN is faster than its conversion to hydrocarbons by Ni catalyst and the interaction between amino group and the carboxylic acid is strong even at high temperatures. Moreover, AP-Ni-MSN-2 catalyst was as active as $Ni_2P$-MSN, which showed less cracking and higher $C_{17}$ and $C_{18}$ yield.

Example 11

Enhancement of HDO Selectivity by Integrated Sequestration-Catalysis Approach

Figure 7:
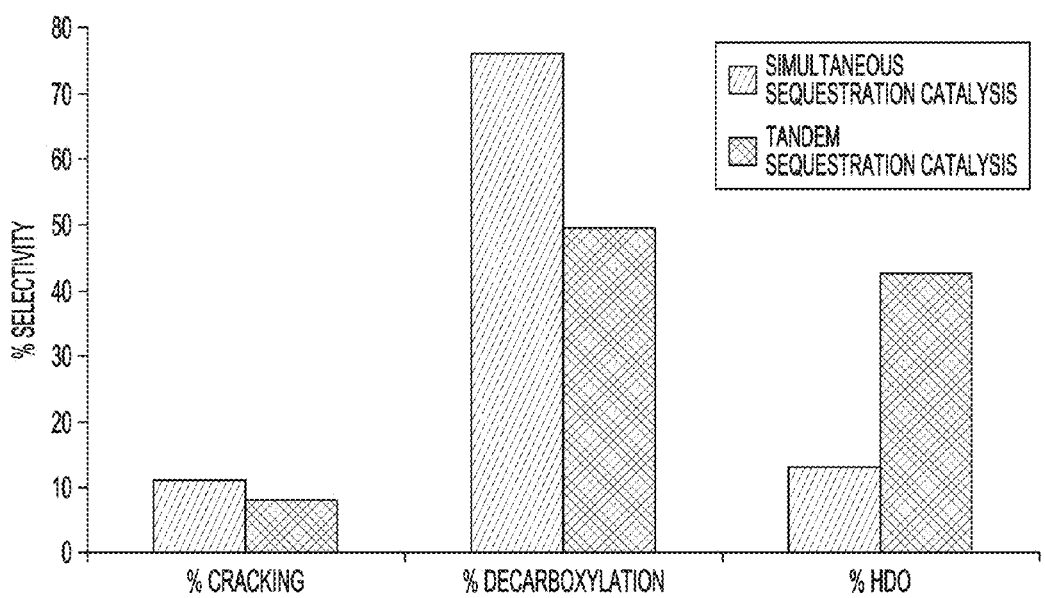
FIG. 7 illustrates the percent selectivity of AP-Ni-MSN-2 catalyst toward various reactions, according to various embodiments.

It was hypothesized that if the residence time of oleic acid near the active Ni catalyst in the mesopores is increased before the catalysis, the chemical processing of oleic acid in the reaction condition should be different than the simultaneous sequestration-catalysis approach discussed earlier. In order to test this hypothesis, at first the oleic acid was sequestered by AP-Ni-MSN-2 catalyst at ambient condition by shaking. The catalyst was separated, air dried and suspended in hexane, which was then processed at reaction condition. Unexpectedly, as compared to the simultaneous sequestration-catalysis method, the HDO selectivity (e.g., $C_{18}$ yield) increased by three-fold with tandem sequestration-catalysis approach, as shown in FIG. 7. To the best of our knowledge, this type of sorbent assisted catalysis has not been explored before. This Example demonstrates that the adsorbent-functionalized catalyst-containing MSN can increase the C:O ratio of a mixture as evident by the increase in $C_{17}$ and $C_{18}$ hydrocarbons, compared to a catalyst not functionalized with adsorbent groups.

Example 12

Selective Sequestration and Hydrotreatment of Microalgae Oil with AP-Ni-MSN

In biodiesel production, the basic catalysts used for the tranesterification of oils with short-chain alcohols can be neutralized by free fatty acids (FFAs), forming soap. Removal of FFAs by selective sequestration on magnetic nanomaterials such as AP-Ni-MSN can provide a valuable alternative environmentally friendly method at least in part due to room temperature adsorption process and separation by magnetic decantation. Moreover, the integration of both aminopropyl functional groups for sequestration of FFAs and magnetic Ni-MSN catalyst for conversion of FFAs to liquid hydrocarbon fuels can be a remarkable alternative for downstream processing of FFA rich renewable feedstocks for bio-fuel production.

Figure 8A:
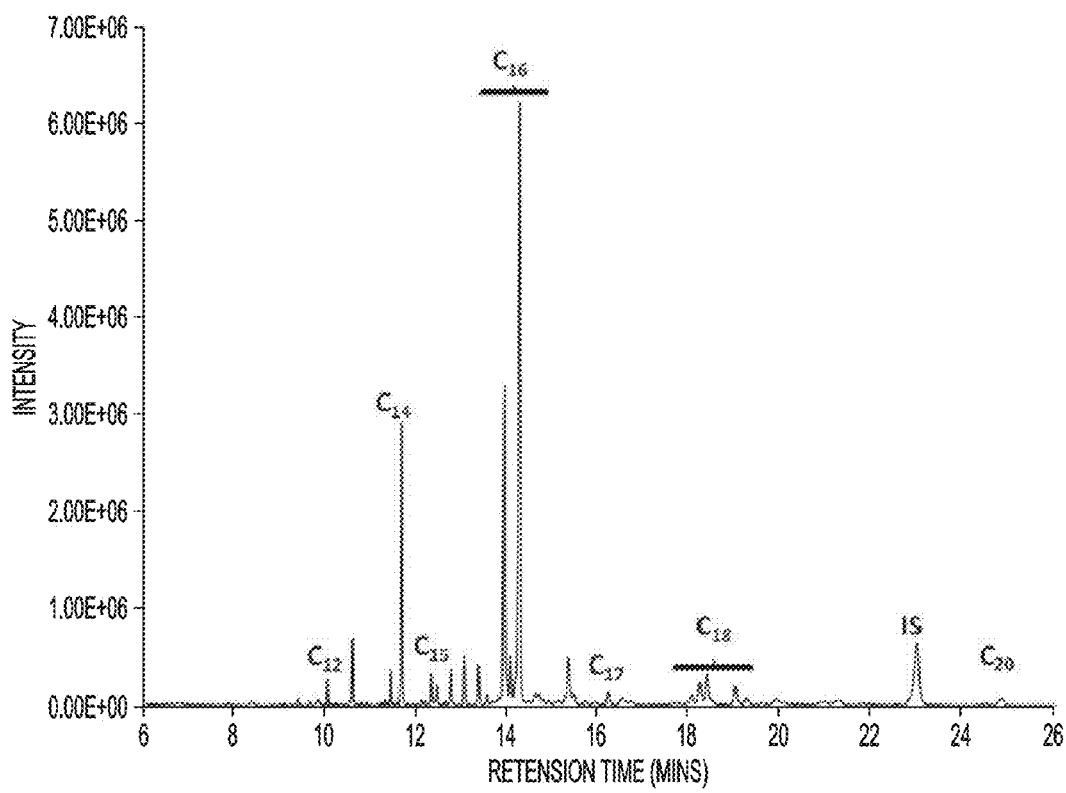
FIG. 8a illustrates the concentration of various fatty acids extracted from microalgae, in accordance with various embodiments.

The microalgae extract in hexanes was first analyzed to ascertain the presence of FFAs. The chain length of FFAs detected in microalgae extract ranges from $C_{12}$ to $C_{20}$ as shown in the FFA profile of microalgae extract in FIG. 8a. The FFAs from these microalgae extract (10 mL) was sequestered with AP-Ni-MSN (10 mg) and subsequently treated at reaction condition for integrated batch reaction. It was demonstrated that 47 wt % of available FFA in microalgae extract was sequestered by AP-Ni-MSN and 66% of those sequestered FFA were converted to liquid hydrocarbons (Table 2). It should be noted that the FFA composition of microalgae extract mostly comprises saturated $C_{16}$ fatty acids (50 wt %) and unsaturated $C_{16}$ fatty acids (30 wt %).

Figure 8B:
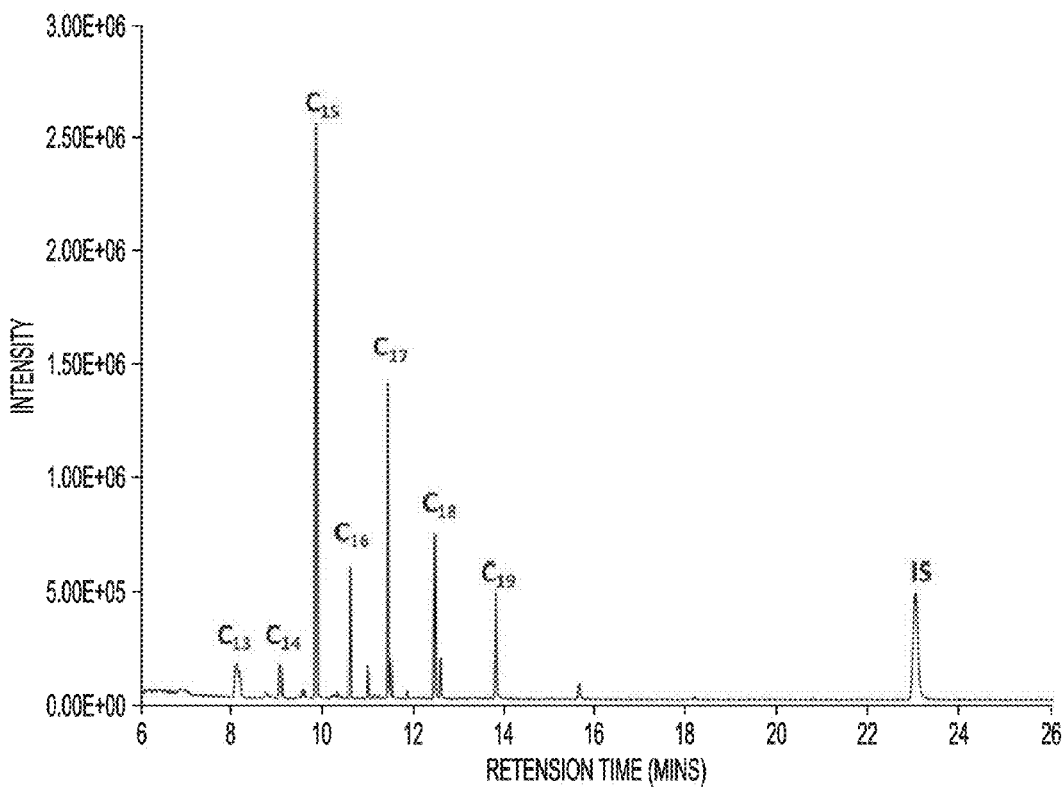
FIG. 8b illustrates the concentration of various hydrocarbons formed by hydrotreating fatty acids sequestered from microalgae using AP-Ni-MSN, in accordance with various embodiments.

Moreover, the fatty acid with $C_{16}$ chain length is also the most sequestered FFAs (68 wt %). As shown in FIG. 8b, n-pentadecane is the major liquid hydrocarbon obtained because of the decarboxylation of sequestered $C_{16}$ FFAs with integrated AP-Ni-MSN catalyst.

TABLE 2

Integrated sequestration catalysis.

| Amount of FFAs present (mg · $L^{-1}$) | Amount of FFAs extracted (mg · $g^{-1}$ of AP-Ni-MSN) | Amount of hydrocarbons (mg · $g^{-1}$ of AP-Ni-MSN) |
|---|---|---|
| 413 | 195 | 95.3 |

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

Additional Embodiments

The present invention provides for the following exemplary embodiments, the numbering of which is not to be construed as designating levels of importance:

Embodiment 1 provides an adsorbent catalytic nanoparticle comprising: at least one adsorbent functional group comprising a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups; and at least one catalytic material.

Embodiment 2 provides the adsorbent catalytic nanoparticle of Embodiment 1, wherein the adsorbent functional group adsorbs fatty acids at a higher rate than it adsorbs at least one of fatty acid esters and triglycerides.

Embodiment 3 provides the adsorbent catalytic nanoparticle of any one of Embodiments 1-2, wherein the adsorbent functional group comprises at least one of an amino($C_{1-10}$) alkyl group and a salt thereof wherein the alkyl unit is covalently bound to the mesoporous nanoparticle.

Embodiment 4 the adsorbent catalytic nanoparticle of any one of Embodiments 1-3, wherein the adsorbent functional group comprises at least one of an aminopropyl group and a salt thereof wherein the propyl unit is covalently bound to the mesoporous nanoparticle.

Embodiment 5 provides the adsorbent catalytic nanoparticle of any one of Embodiments 1-4, wherein the adsorbent functional group is present in a concentration of about 0.01 mmol-50 mmol per gram of the mesoporous nanoparticle.

Embodiment 6 provides the adsorbent catalytic nanoparticle of any one of Embodiments 1-5, wherein the adsorbent functional group is present in a concentration of about 0.1 mmol-15 mmol per gram of the mesoporous nanoparticle.

Embodiment 7 provides the adsorbent catalytic nanoparticle of any one of Embodiments 1-6, wherein the adsorbent catalytic nanoparticle catalyzes decarboxylation and hydrodeoxygenation of a free fatty acid at a higher rate than a mesoporous nanoparticle not having the adsorbent functional group bound thereto.

Embodiment 8 provides the adsorbent catalytic nanoparticle of any one of Embodiments 1-7, wherein the adsorbent catalytic nanoparticle catalyzes cracking of a free fatty acid at a lower rate than a corresponding mesoporous nanoparticle not having the adsorbent functional group bound thereto.

Embodiment 9 provides the adsorbent catalytic nanoparticle of any one of Embodiments 1-8, wherein the adsorbent functional group is present in a concentration of at least about 0.5 mmol per gram of the mesoporous nanoparticle.

Embodiment 10 provides the adsorbent catalytic nanoparticle of any one of Embodiments 1-9, wherein the percent selectivity of the adsorbent catalytic nanoparticle toward catalyzation of cracking of a free fatty acid is about 10-30% of the selectivity toward catalyzation of cracking of the free fatty acid of a corresponding mesoporous nanoparticle including the catalytic material but not having the adsorbent functional group bound thereto.

Embodiment 11 provides the adsorbent catalytic nanoparticle of any one of Embodiments 1-10, wherein the percent selectivity of the adsorbent catalytic nanoparticle toward catalyzation of cracking of a free fatty acid is about 15-25% of the selectivity toward catalyzation of cracking of the free fatty acid of a corresponding mesoporous nanoparticle including the catalytic material but not having the adsorbent functional group bound thereto.

Embodiment 12 provides the adsorbent catalytic nanoparticle of any one of Embodiments 1-11, wherein the percent selectivity of the adsorbent catalytic nanoparticle toward catalyzation of decarboxylation of a free fatty acid is about 200-400% of the selectivity toward catalyzation of decarboxylation of the free fatty acid of a corresponding mesoporous nanoparticle including the catalytic material but not having the adsorbent functional group bound thereto.

Embodiment 13 provides the adsorbent catalytic nanoparticle of any one of Embodiments 1-12, wherein the percent selectivity of the adsorbent catalytic nanoparticle toward catalyzation of decarboxylation of a free fatty acid is about 250-350% of the selectivity toward catalyzation of decarboxylation of the free fatty acid of a corresponding mesoporous nanoparticle including the catalytic material but not having the adsorbent functional group bound thereto.

Embodiment 14 provides the adsorbent catalytic nanoparticle of any one of Embodiments 1-13, wherein the percent selectivity of the adsorbent catalytic nanoparticle toward catalyzation of hydrodeoxygenation of a free fatty acid is about 100-800% of the selectivity toward catalyzation of hydrodeoxygenation of the free fatty acid of a corresponding mesoporous nanoparticle including the catalytic material but not having the adsorbent functional group bound thereto.

Embodiment 15 provides the adsorbent catalytic nanoparticle of any one of Embodiments 1-14, wherein the percent selectivity of the adsorbent catalytic nanoparticle toward catalyzation of hydrodeoxygenation of a free fatty acid is about 200-600% of the selectivity toward catalyzation of hydrodeoxygenation of the free fatty acid of a corresponding mesoporous nanoparticle including the catalytic material not having the adsorbent functional group bound thereto.

Embodiment 16 provides the adsorbent catalytic nanoparticle of any one of Embodiments 1-15, wherein the catalytic material comprises catalytic nanoparticles.

Embodiment 17 provides the adsorbent catalytic nanoparticle of any one of Embodiments 1-16, wherein the catalytic material is a hydrotreatment catalyst.

Embodiment 18 provides the adsorbent catalytic nanoparticle of any one of Embodiments 1-17, wherein the catalytic material comprises at least one of a cracking catalyst, a decarboxylation catalyst, and a hydrodeoxygenation catalyst.

Embodiment 19 provides the adsorbent catalytic nanoparticle of any one of Embodiments 1-18, wherein the catalytic material comprises at least one of nickel, nickel phosphide, iron, iron oxide, rhodium, ruthenium, gold, cobalt, cobalt oxide, palladium, platinum, and molybdenum.

Embodiment 20 provides the adsorbent catalytic nanoparticle of any one of Embodiments 1-19, wherein the catalytic material is located within the pores of the mesoporous nanoparticle.

Embodiment 21 provides the adsorbent catalytic nanoparticle of any one of Embodiments 1-20, wherein the catalytic material is evenly distributed within the pores of the mesoporous nanoparticle.

Embodiment 22 provides the adsorbent catalytic nanoparticle of any one of Embodiments 1-21, wherein the catalytic material is crystalline.

Embodiment 23 provides the adsorbent catalytic nanoparticle of any one of Embodiments 1-22, wherein the adsorbent catalytic nanoparticle comprises about 1-30 wt % of the catalytic material.

Embodiment 24 provides the adsorbent catalytic nanoparticle of any one of Embodiments 1-23, wherein the adsorbent catalytic nanoparticle comprises about 1-30 wt % nickel.

Embodiment 25 provides the adsorbent catalytic nanoparticle of any one of Embodiments 1-24, wherein the adsorbent catalytic nanoparticle comprises about 5-15 wt % nickel.

Embodiment 26 provides the adsorbent catalytic nanoparticle of any one of Embodiments 1-25, wherein the adsorbent catalytic nanoparticle has a diameter of about 50 nm-1200 nm.

Embodiment 27 provides the adsorbent catalytic nanoparticle of any one of Embodiments 1-26, wherein the adsorbent catalytic nanoparticle has a surface area of about 100 $m^2/g$-1000 $m^2/g$.

Embodiment 28 provides the adsorbent catalytic nanoparticle of any one of Embodiments 1-27, wherein the adsorbent catalytic nanoparticle has a surface area of approximately 150 $m^2/g$ to approximately 375 $m^2/g$.

Embodiment 29 provides the adsorbent catalytic nanoparticle of any one of Embodiments 1-28, wherein the adsorbent catalytic nanoparticle has a pore size of approximately 5 nm to approximately 15 nm.

Embodiment 30 provides the adsorbent catalytic nanoparticle of any one of Embodiments 1-29, wherein the adsorbent catalytic nanoparticle is magnetic.

Embodiment 31 provides the adsorbent catalytic nanoparticle of any one of Embodiments 1-30, wherein the adsorbent catalytic nanoparticle comprises at least one of $Fe_2O_3$ and $Fe_3O_4$.

Embodiment 32 provides the adsorbent catalytic nanoparticle of any one of Embodiments 1-31, wherein the adsorbent catalytic nanoparticle comprises an ordered silicon oxide matrix with hexagonal symmetry.

Embodiment 33 provides a method comprising: combining at least one adsorbent catalytic nanoparticle of any one of Embodiments 1-32 with at least one first molecule that is selectively adsorbed by the adsorbent functional group, to provide a mixture.

Embodiment 34 provides the method of Embodiment 33, wherein the first molecule is a fatty acid.

Embodiment 35 provides the method of any one of Embodiments 33-34, comprising combining the mixture with a first reagent, under conditions so that the catalytic material in the adsorbent catalytic nanoparticle catalyzes a chemical transformation of the first molecule.

Embodiment 36 provides the method of Embodiment 35, wherein the first reagent comprises hydrogen gas.

Embodiment 37 provides the method of Embodiment 36, wherein the pressure of the hydrogen is controlled to be 1 bar-1000 bar.

Embodiment 38 provides the method of any one of Embodiments 36-37, wherein the pressure of the hydrogen is controlled to be about 10-100 bar.

Embodiment 39 provides the method of any one of Embodiments 36-38, wherein the temperature of the hydrogen is controlled to 150-1000° C.

Embodiment 40 provides the method of any one of Embodiments 36-39, wherein the temperature of the hydrogen is controlled to be about 250-350° C.

Embodiment 41 provides the method of any one of Embodiments 35-40, wherein the chemical transformation of the first molecule comprises at least one of cracking, decarboxylation, and hydrodeoxygenation.

Embodiment 42 provides the method of any one of Embodiments 33-41, wherein combining the adsorbent catalytic nanoparticle with the first molecule comprises combining the adsorbent catalytic nanoparticle with a solution comprising the first molecule, to provide the mixture.

Embodiment 43 provides the method of Embodiment 42, wherein the solution further comprises at least one second molecule that is at least one of a) not adsorbed by the adsorbent functional group and b) adsorbed by the adsorbent functional group at a lower rate than the first molecule is adsorbed by the adsorbent functional group.

Embodiment 44 provides the method of Embodiment 43, wherein the second molecule is at least one of a fatty acid ester and a triglyceride.

Embodiment 45 provides the method of any one of Embodiments 43-44, wherein the second molecule is at least one of a $C_{1-50}$ fatty acid $C_{1-50}$ ester and a triglyceride having $C_{1-50}$ fatty acid groups.

Embodiment 46 provides the method of any one of Embodiments 33-45, wherein the first molecule is a fatty acid.

Embodiment 47 provides the method of any one of Embodiments 33-46, wherein the first molecule is a $C_{1-50}$ fatty acid.

Embodiment 48 provides the method of any one of Embodiments 42-47, comprising separating the adsorbent catalytic nanoparticle having the first molecule adsorbed thereto from the mixture.

Embodiment 49 provides the method of Embodiment 48, comprising at least one of using and selling the separated mixture as a feedstock for generating biodiesel.

Embodiment 50 provides the method of any one of Embodiments 48-49, comprising combining the separated adsorbent catalytic nanoparticle with a first reagent under conditions so that the catalytic material in the adsorbent catalytic nanoparticle catalyzes a chemical transformation of the first molecule.

Embodiment 51 provides the method of Embodiment 50, wherein the first reagent comprises hydrogen gas.

Embodiment 52 provides the method of Embodiment 51, wherein the pressure of the hydrogen is controlled to be about 1 bar-1000 bar.

Embodiment 53 provides the method of any one of Embodiments 51-52, wherein the pressure of the hydrogen is controlled to be about 10-100 bar.

Embodiment 54 provides the method of any one of Embodiments 51-53, wherein the temperature of the combined separated adsorbent catalytic nanoparticle and the hydrogen is controlled to be about 150-1000° C.

Embodiment 55 provides the method of any one of Embodiments 51-54, wherein the temperature of the combined separated adsorbent catalytic nanoparticle and the hydrogen is controlled to be about 250-350° C.

Embodiment 56 provides the method of any one of Embodiments 50-55, wherein the chemical transformation of the first molecule comprises at least one of cracking, decarboxylation, and hydrodeoxygenation.

Embodiment 57 provides the method of Embodiment 56, comprising at least one of using and selling the product of the chemical transformation of the first molecule as a fuel.

Embodiment 58 provides a method comprising: combining at least one adsorbent functional group comprising a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups; and at least one catalytic material; and combining the mixture with hydrogen gas under conditions so that the catalytic material at least one of cracks, decarboxylates, and hydrodeoxygenates at least some of the free fatty acid.

Embodiment 59 provides a method comprising: combining at least one adsorbent catalytic nanoparticle with a solution comprising a free fatty acid and at least one of a fatty acid ester and a triglyceride, to provide a mixture, the adsorbent catalytic nanoparticle comprising at least one adsorbent functional group comprising a functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to a mesoporous silica nanoparticle, and wherein the $C_1$-$C_{20}$ alkyl groups of the amino($C_1$-$C_{20}$)alkyl group are independently optionally interrupted by one or two —NH— groups; and at least one catalytic material; separating the adsorbent catalytic nanoparticle having the first molecule adsorbed thereto from the mixture; and combining the separated adsorbent catalytic nanoparticle with hydrogen gas so that the catalytic material in the adsorbent catalytic nanoparticle catalyzes a chemical transformation of the fatty acid comprising at least one of cracking, decarboxylation, and hydrodeoxygenation.

Embodiment 60 provides the apparatus or method of any one or any combination of Embodiments 1-59 optionally configured such that all elements or options recited are available to use or select from.

What is claimed is:

1. An adsorbent catalytic nanoparticle comprising:
at least one adsorbent functional group selected from the group consisting of an amino($C_1$-$C_{20}$)alkyl group or a salt thereof, a ($C_1$-$C_{20}$)alkyl carboxylic acid group or a salt thereof, a ($C_1$-$C_{20}$)alkyl sulfonic acid group or a salt thereof, and a perfluoro($C_1$-$C_{20}$)alkyl group, wherein the alkyl unit of the aminoalkyl group, the alkyl carboxylic acid group, the alkyl sulfonic acid group, and of the perfluoroalkyl group is covalently bound to the adsorbent catalytic nanoparticle, wherein the adsorbent catalytic nanoparticle is a mesoporous silica nanoparticle, and wherein the ($C_1$-$C_{20}$)alkyl groups of the amino($C_1$-$C_{20}$)alkyl group are independently optionally interrupted by one or two —NH— groups; and
at least one catalytic material in pores of the mesoporous silica nanoparticle, the at least one catalytic material comprising nickel, nickel phosphide, elemental iron, rhodium, ruthenium, gold, cobalt, cobalt oxide, palladium, platinum, molybdenum, or a combination thereof.

2. The adsorbent catalytic nanoparticle of claim 1, wherein the adsorbent functional group adsorbs fatty acids at a higher rate than it adsorbs at least one of fatty acid esters and triglycerides.

3. The adsorbent catalytic nanoparticle of claim 1, wherein the adsorbent functional group comprises at least one of an amino($C_{1-10}$)alkyl group and a salt thereof wherein the alkyl unit is covalently bound to the mesoporous silica nanoparticle.

4. The adsorbent catalytic nanoparticle of claim 1, wherein the adsorbent functional group is present in a concentration of about 0.01 mmol to about 50 mmol per gram of the mesoporous silica nanoparticle.

5. The adsorbent catalytic nanoparticle of claim 1, wherein the adsorbent catalytic nanoparticle catalyzes decarboxylation and hydrodeoxygenation of a free fatty acid at a higher rate than a mesoporous nanoparticle not having the adsorbent functional group bound thereto.

6. The adsorbent catalytic nanoparticle of claim 1, wherein the adsorbent catalytic nanoparticle catalyzes cracking of a free fatty acid at a lower rate than a corresponding mesoporous silica nanoparticle not having the adsorbent functional group bound thereto.

7. The adsorbent catalytic nanoparticle of claim 1, wherein the catalytic material is a hydrotreatment catalyst.

8. The adsorbent catalytic nanoparticle of claim 1, wherein the adsorbent catalytic nanoparticle comprises about 1 wt % to about 30 wt % of the catalytic material.

9. The adsorbent catalytic nanoparticle of claim 1, wherein the mesoporous silica nanoparticle is magnetic.

10. The adsorbent catalytic nanoparticle of claim 1, wherein the mesoporous silica nanoparticle comprises an ordered silicon oxide matrix with hexagonal symmetry.

11. A method comprising:
combining at least one adsorbent catalytic nanoparticle of claim 1 with at least one first molecule that is selectively adsorbed by the adsorbent functional group, to provide a mixture.

12. The method of claim 11, comprising combining the mixture with a first reagent, under conditions so that the catalytic material in the adsorbent catalytic nanoparticle catalyzes a chemical transformation of the first molecule.

13. The method of claim 11, wherein combining the adsorbent catalytic nanoparticle with the first molecule comprises combining the adsorbent catalytic nanoparticle with a solution comprising the first molecule, to provide the mixture, wherein the solution further comprises at least one second molecule that is at least one of a) not adsorbed by the adsorbent functional group and b) adsorbed by the adsorbent functional group at a lower rate than the first molecule is adsorbed by the adsorbent functional group.

14. The method of claim 13, wherein the second molecule is at least one of a fatty acid ester and a triglyceride.

15. The method of claim 11, wherein the first molecule is a fatty acid.

16. The method of claim 13, comprising separating the adsorbent catalytic nanoparticle having the first molecule adsorbed thereto from the mixture.

17. The method of claim 16, comprising combining the separated adsorbent catalytic nanoparticle with a first reagent under conditions so that the catalytic material in the adsorbent catalytic nanoparticle catalyzes a chemical transformation of the first molecule.

18. A method comprising:
combining at least one adsorbent catalytic nanoparticle of claim 1 with a free fatty acid, to provide a mixture; and
combining the mixture with hydrogen gas under conditions so that the catalytic material at least one of cracks, decarboxylates, and hydrodeoxygenates at least some of the free fatty acid.

19. A method comprising:
combining at least one adsorbent catalytic nanoparticle of claim 1 with a solution comprising a free fatty acid and at least one of a fatty acid ester and a triglyceride, to provide a mixture;
separating the adsorbent catalytic nanoparticle having the first molecule adsorbed thereto from the mixture; and
combining the separated adsorbent catalytic nanoparticle with hydrogen gas so that the catalytic material in the adsorbent catalytic nanoparticle catalyzes a chemical transformation of the fatty acid comprising at least one of cracking, decarboxylation, and hydrodeoxygenation.

* * * * *